United States Patent
Kovalenko

(10) Patent No.: US 7,125,517 B2
(45) Date of Patent: Oct. 24, 2006

(54) SYSTEMS AND METHODS FOR DETECTION OF ANALYTES IN BIOLOGICAL FLUIDS

(75) Inventor: Victor A. Kovalenko, Saco, ME (US)

(73) Assignee: Immunetics, Inc., Boston, MA (US)

( * ) Notice: Subject to any disclaimer, the term of this patent is extended or adjusted under 35 U.S.C. 154(b) by 0 days.

(21) Appl. No.: 10/914,492

(22) Filed: Aug. 9, 2004

(65) Prior Publication Data

US 2005/0042696 A1   Feb. 24, 2005

Related U.S. Application Data

(62) Division of application No. 10/138,654, filed on May 3, 2002.

(60) Provisional application No. 60/334,807, filed on Nov. 15, 2001, provisional application No. 60/288,597, filed on May 3, 2001.

(51) Int. Cl.
*B01L 3/00* (2006.01)

(52) U.S. Cl. .......................... 422/61; 435/7.1; 435/7.9; 435/243; 436/518

(58) Field of Classification Search ................ 435/7.1, 435/7.9, 243; 436/518
See application file for complete search history.

(56) References Cited

U.S. PATENT DOCUMENTS

| | | | |
|---|---|---|---|
| 4,228,237 A | 10/1980 | Hevey et al. ................... 435/7 |
| 4,298,685 A | 11/1981 | Parikh et al. ................... 435/7 |
| 4,444,879 A * | 4/1984 | Foster et al. ................ 435/7.95 |
| 4,772,691 A * | 9/1988 | Herman ...................... 536/24.3 |
| 4,778,751 A | 10/1988 | El Shami et al. ................ 435/7 |
| 4,945,042 A | 7/1990 | Geiger et al. ................... 435/7 |
| RE34,312 E | 7/1993 | Geiger et al. |
| 5,236,849 A | 8/1993 | Ishikawa ..................... 436/540 |
| 5,277,589 A | 1/1994 | Schmitt et al. |
| 5,312,730 A | 5/1994 | Piran et al. ................. 535/7.92 |
| 5,391,272 A | 2/1995 | O'Daly et al. .......... 204/153.12 |
| 5,534,132 A | 7/1996 | Vreeke et al. ............. 205/777.5 |
| 5,595,878 A | 1/1997 | Sood et al. ..................... 435/6 |
| 5,705,338 A | 1/1998 | Piran et al. ..................... 435/6 |
| 5,776,702 A | 7/1998 | Schmitt et al. |
| 5,895,750 A * | 4/1999 | Mushahwar et al. ......... 435/7.5 |
| 5,919,633 A | 7/1999 | Tausk et al. |
| 5,972,199 A | 10/1999 | Heller et al. ............. 205/777.5 |
| 5,981,203 A | 11/1999 | Meyerhoff et al. ......... 435/7.92 |
| 5,989,806 A | 11/1999 | Brust ............................. 435/5 |
| 6,030,770 A | 2/2000 | Brust ............................. 435/5 |
| 6,121,006 A | 9/2000 | Glover ....................... 435/7.2 |
| 6,489,129 B1 | 12/2002 | Faatz et al. |
| 6,645,732 B1 | 11/2003 | Faatz et al. |
| 6,828,110 B1 | 12/2004 | Lee et al. |
| 2002/0082386 A1 | 6/2002 | Mangold et al. |

FOREIGN PATENT DOCUMENTS

WO   WO 97/42221   11/1997

OTHER PUBLICATIONS

International Preliminary Examination Report; mailed on Nov. 10, 2003.
International Search Report, completed on Jul. 15, 2002 and mailed on Aug. 22, 2002.
Morissette, et al., Rapid and Sensitive Sandwich Enzyme-Linked Immunosorbent Assay for Detection of Staphylococcal Enterotoxin B in Cheese, Applied and Environmental Microbiology, Mar. 1991, vol. 57, No. 3, pp. 836-842.
Liang, Fang Ting, et al., Sensitive and Specific Serodiagnosis of Lyme Disease by Enzyme-Linked Immunosorbent Assay with a Peptide Based on an Immunodominant Conserved Region of *Borrelia burgdorferi* VlsE, Journal of Clinical Microbiology, vol. 37, No. 12, Dec. 1999, pp. 3990-3996.
Mathiesen, Marianne J., et al., Peptide-Based OspC Enzyme-Linked Immunosorbent Assay for Serodiagnosis of Lyme Borreliosis, Journal of Clinical Microbiology, vol. 36, No. 12, Dec. 1998, pp. 3474-3479.

\* cited by examiner

*Primary Examiner*—James Housel
*Assistant Examiner*—Deborah A. Davis
(74) *Attorney, Agent, or Firm*—Isabelle M. Clauss; Foley Hoag LLP

(57) ABSTRACT

The invention provides a heterogeneous immunoassay for detection of antibodies and antigens based on specific antigen-antibody immune complex formation with multiple antigen-bearing conjugate components. The invention further provides means for optimizing the assay format for the detection of both low and high-affinity antibodies, and provides means for quantitative detection of both antibody and the corresponding antigen present in a sample.

13 Claims, 15 Drawing Sheets

SYSTEMS AND METHODS FOR DETECTION OF ANALYTES IN BIOLOGICAL FLUIDS

RELATED U.S. APPLICATION

This application is a divisional application of U.S. Ser. No. 10/138,654, filed May 3, 2002, which is hereby incorporated herein by reference.

FIELD OF THE INVENTION

The present invention relates to an immunochemical assay and method for qualitative or quantitative detection of analytes in biological fluids.

BACKGROUND ART

Antibodies are protein molecules which specifically bind antigens that initiate the formation of the antibodies. Antibodies are produced by B-lymphocytes and plasma cells, and are present in blood plasma (as secretory antibodies or cell bound), lymphatic fluids, cerebrospinal fluid, mucus and other extracellular secretions (e.g., saliva), and in some instances, urine. Assays for antibodies have been widely applied to the examination and diagnosis of many infections, and autoimmune and allergic conditions.

There are currently several known immunoglobulin classes, IgG, IgM, IgA, IgE and IgD. These immunoglobulins are involved in different types of immune responses, and their involvements are dependent, for example, on antigen structures, type of organisms which bear these antigens, time after immunization, and presence of other antigenic molecules in the microorganisms. It is believed that antibody classes important for serological testing and secretory immunoglobulins contain two or more identical antigen-combining sites. In particular, it is believed that there are two sites for IgG and IgE, four for IgA, and up to 10 for IgM. This mean that at least two antigen molecules or specific antigenic (epitopic) substances can bind simultaneously to one antibody molecule.

It should be noted that affinity of antibodies to specific antigens may not be constant. Beside the spectrum of polyclonal antibodies which can differ in affinity at varying stages of an immune response depending on the particular pathogen/immunogen, affinity of antibodies can change with time, from low to high affinity, for instance, during the antibody maturation process. Moreover, several antibody classes can simultaneously recognize the same antigen. In the case of bacterial, viral, protozoan, parasitic, or fungal infection, the IgM class can appear at the early stages of an immune response, usually as antibody with a low affinity constant, while the IgG class can appear later in the immune response. For serological testing constant, while the IgG class can appear later in the immune response. For serological testing of many infections, the ability to detect antibodies at the earliest stages of seroconversion can be very important in determining a treatment. Because the IgM class antibodies often appear during the early stages of infection, their presence is often considered as a serological indication of early stage of infection.

Antibodies can be detected using a variety of immunoassay protocols. Among conventional methods, the most widely used works on principles of solid phase immunoassay using immobilized antigens and secondary class-specific anti-immunoglobulins conjugated with detector labels, such as, enzyme, fluorophores, chemiluminescent, metal sols, dyed polymeric particles, or labeled proteins which bind to immunoglobulins (protein A and G). A disadvantage of such a method is that a falsely positive result can be obtained due to non-specific and cross-reactive reactions related to simple adsorption of non-specific antibodies on coated solid phase, or the presence of unwanted antigenic substances in antigens used for adsorption on solid phase. This can happen even in case of using relatively pure antigens obtained by methods of recombinant technology. Moreover, the presence of, for instance, autoantibodies, rheumatoid factor, or polyspecific/polyreactive antibodies, can lead to false results. Even in case of using very specific small peptide antigens, false positives can arise as result of contaminations in the reagents used for immobilization on solid phase.

In order to reduce the occurrence of false positives, steps, such as, selection of sample dilution, incubation time, temperature, and diluents used, have been taken to reduce potential cross-reactive reactions. However, such steps can require the application of many serological tests and can reduce detection sensitivity. For example, in a solid phase immunoassay using solid phase immobilized antigens, the presence of conjugates antigen-specific antibodies with detector label can compete with antibodies in a sample to be detected to bind with the immobilized antigens. As a result, although this competitive test is relatively simple and may be less susceptible to non-specific reactions, its sensitivity for detection can be relatively low.

In another immunoassay for specific antibody detection based on competitive binding, a specific antibody may be immobilized in a solid phase. However, during incubation, labeled antigens in the sample and the antibody to be detected in the sample can compete to bind with the immobilized antibody. As with the previous example, sensitivity of detection may be affected due to competitive binding, and as a result, may require a significant amount of pure anti-antigen antibodies for use.

In another immunoassay, the solid phase may be coated with a class specific immunoglobulins. Labeled antigens may be used in the sample of the antibody to be detected to form an immune complex with the class specific immunoglobulins in the solid phase. One disadvantage of this immunoassay is the limited binding capacity of the class specific immunoglobulins in the solid phase, which can limit the sensitivity of specific antibody detection.

A further variation of solid phase immunoassay involves the use of solid phase coated antigens to capture specific antibody and subsequent detection of captured/bound antibody with a labeled antigen. However, a prozoning phenomenon may be a problem for this approach. In particular, the density of antigen on solid phase should be carefully optimized to protect the antibody from binding with the solid phase antigen through all combining sites (e.g., IgG class) on the antibody, which reduce number of sites available on the antibody to bind with labeled antigen. A second incubation with labeled antigen is described in U.S. Pat. No. 6,121,006 as a way for increasing sensitivity of this type of assay.

U.S. Pat. No. 6,030,770 discloses a method for antibody detection using labeled antigen and a solid phase capture system. In this method, the solid phase comprises immobilized antigens and anti-immunoglobulin antibodies introduced into the capture system through an additional bridge. The bridge, as disclosed, includes analyte-specific antibodies capable of recognizing ligand-labeled anti-species class specific antibodies.

U.S. Pat. No. 4,778,751 discloses a method for detection of circulating antibodies, which method is based on the use of a ligand-labeled polymeric matrix. In this method, the matrix is conjugated with multiple antigen molecules, a ligand-binding partner immobilized on solid phase, and anti-immunoglobuline detector reagent.

In U.S. Pat. No. 4,945,042, a three reagents antibody detection system is disclosed. The detection system, as disclosed, comprises two components of a specific binding pair. One component is included in the capture system as a conjugate of StrAv with thermo polymerized BSA of anti-immunoglobulin antibodies, while the second component is conjugated to the antigen. A third reagent is labeled and is a conjugate of the antigen.

U.S. Pat. No. 5,236,849 discloses a detection method utilizing an antigen containing simultaneously two different labels belonging to two affinity pairs, each with its counterparts distributed between separate solid phases. This approach permits for significant reduction of non-specific reaction by using immune-complex transfer (dissociation-recapture) for detection in a second container.

Lyphophilic bridges, such as liposomes or some other reversible bridge, are disclosed in U.S. Pat. Nos. 5,312,730 and 5,705,338 as a way to dissociate an immune complex from a first solid phase to permit transfer into a second solid phase for detection.

Small peptide antigens, containing specific epitopes, mono or limited amount, can be powerful instrument for development of highly specific serological test. The role of these peptides, whether obtained by chemical synthesis or recombinant technology, have become increasingly important. However, affinity of antibodies against these small epitopes is sometimes lower than the affinity to a sequence in whole protein. Moreover, affinity of antibodies to selected peptide antigens can vary due to the presence of various strains of pathogens and its genetic variability. Accordingly, it is desirable to provide simple methods, which can permit the detection of antibodies that may have low affinity to selected epitopes.

SUMMARY OF INVENTION

The present invention provides, in one embodiment, a simple heterogeneous immunoassay for detection of antibodies based on specific antigen-antibody immune complex formation with dually labeled antigen.

In another embodiment, the present invention provides methods for detection of antibodies against peptide epitopes and haptens or detection of other analytes with multiple identical binding epitopes. In this manner, the method of the present invention can permit detection of, for example, multiple antibody classes in one sample, including antibody with a low affinity constant.

In another embodiment, the present invention provides a simplified method for sample preparation, thereby allowing the assays being carried out to be insensitive to sample dilution, while eliminating factors which can lead to various non-specific reactions and false positives frequently seen in conventional serological tests using anti-immunoglobulin conjugates.

The method of the present invention can be used in a variety of assay formats, including ELISA, dot-blot, flow-through (e.g., immunoconcentration and immunofiltration), and lateral flow, including the possibility for quantitative determination.

In accordance with one embodiment, the present provides a method for detecting an antibody that binds to an antigen or hapten in a sample. The method includes providing a first component having a ligand linked to a solid phase adsorbing composition through a chemical spacer. In an embodiment, the ligand may be biotin, the solid phase adsorbing composition may be albumin and the spacer may be polyethylene glycol. Also provided is a second component having a ligand-binding moiety and the antigen or hapten that binds the antibody. The ligand-binding moiety in an embodiment can be avidin or streptavidin. A third component can be provided comprising an antigen or hapten and a label. The label, in an embodiment, may be one of the following, an enzyme, a fluorescent probe, a chemiluminescent probe, a metal, a non-metal colloidal particle, a polymeric dye particle, and a pigment molecule. The method permits contacting the first component with a solid phase, so as to immobilize the first component. Subsequently, the antibody sample is contacted with the first, second and third components to allow the third component to form an immune complex with the first and second components by binding to the second component through the antibody present in the antibody sample. Thereafter, uncomplexed third component may be separated from the solid phase and the label present in the immune complex may be detected. The detection of the label indicates the presence of the antibody in the antibody sample, and thus the detection of the antibody in the sample.

The present invention also provides, in one embodiment, a composition of matter comprising a ligand linked to a solid phase adsorbing composition through a chemical spacer. In an embodiment, the ligand may be biotin, the solid phase adsorbing composition may be albumin and the spacer may be polyethylene glycol.

The present invention further provides, in an embodiment, a kit comprising a first component having a ligand linked to a solid phase adsorbing composition through a chemical spacer. The kit also includes a second component having a ligand-binding moiety and the antigen or hapten that binds the antibody, and a third component comprising an antigen or hapten and a label. The kit can further include an antibody standard.

DETAILED DESCRIPTION OF SPECIFIC EMBODIMENTS

The present invention provides, in one embodiment, an immunochemical method and reagents for qualitative or quantitative detection of analytes in biological fluids, including detection of antibodies to small antigens, epitopes, peptides or haptens.

The present method, in one embodiment, can be based on the ability of an antibody to bind at least two molecules of the same antigenic substance, due to the presence of at least two specific, substantially identical antigen-binding sites on the antibody. For instance, the IgG class has two identical binding sites, while the IgM class has up to 10 identical binding sites.

Figure 15:
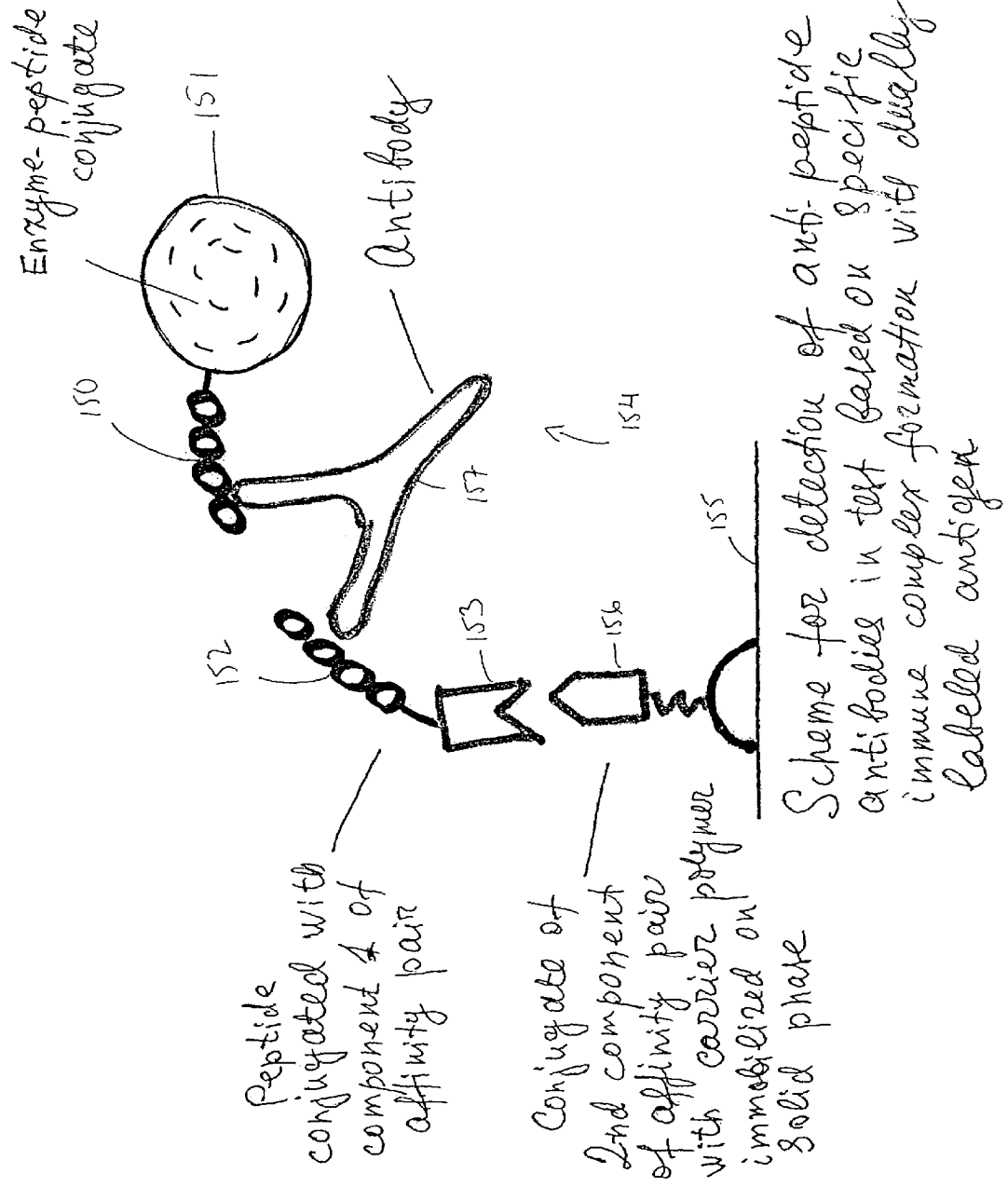
FIG. 15 illustrates a schematic diagram showing the molecular interactions underlying the immunoassays of the present invention.

The principle of antibody detection in the present assay involves formation in solution of a specific immune complex between the antibody to be detected and two molecules of antigen/hapten bearing two different labels. As shown in FIG. 15, one molecule 150 of antigen/hapten may be conjugated with a detector label 151, while a second molecule 152 may be conjugated to a component 153 of a high-affinity pair (e.g., biotin-streptavidin) that allows specific capture of the ternary immune complex 154 thus formed onto a solid phase 155 coated with the other component 156 of the affinity pair. The two conjugates 150 and 152 may be added as a mixture to the sample being analyzed. In principle, one conjugate 150 can bind to one antigen-binding site of the antibody molecule 157 to be detected, while the second conjugate 152 can bind to the other antigen-binding site on the same antibody molecule 157. Ternary complex 154 thus formed is bound to the solid phase 155 via the specific interaction of the second conjugate 152 and its associated partner 153 of the affinity pair with the other affinity partner 156 immobilized on the solid phase 155. An appropriate detection method (enzymatic or other) can then be applied to detect binding of the antibody-antigen complex. A single washing step may be needed to remove excess reagent prior to quantitation of bound detector label. Most known types of labels (enzymatic, fluorescent, chemiluminescent, colloidal gold, other colloids, colored particles etc.) used in various immunoassays can be utilized in tests based on this principle.

Furthermore, the detection principle employ by the present invention may be applicable to various test formats. For example, it can be shown that the same reagents used for creation of a microplate C6 ELISA can function effectively in membrane ELISA formats, including rapid tests (performed in 5–10 min), in which sensitivity equal to or higher than that of the microplate ELISA format was demonstrated. Moreover, the present method can also be useful in antibody detection using rapid immunofiltration and immunochromatographic assay techniques while exhibiting very low background and non-specific reactions. The method of the present invention may also be especially suitable for application in immunochromatographic serological tests.

The present method, in accordance with an embodiment, can be substantially free from most interfering factors related to cross-reactivity problems, can work effectively with undiluted serum/plasma samples, can provide extremely low signal for normal samples, and has significantly higher analytical sensitivity. Diagnostic sensitivity and specificity may also be increased with the present method.

Assay protocols for use with the present invention can be relatively simple and more convenient, with short turn-around time. For instance, an entire test can be performed within 30 minutes. The need for sample dilution may also be eliminated, as undiluted sample and conjugates can be mixed directly in wells of a coated plate, followed by a single wash step. As such, testing of multiple samples can be especially convenient because of the insensitivity of results to prolonged incubation between additions of sample and conjugates.

In addition, a broad range of linearity of absorbance (OD) values, covering almost the full scale of a typical ELISA reader in optimized assay conditions may be achieved with a method of the present invention, making such method valuable for quantitative determination of anti-peptide antibody concentration. For instance, the detection limit for IgG antibody using the method of the present invention with HRP label and commercially available tetramethylbenzidene (TMB)-based chromogenic substrates can be as low as 5 ng/ml in a 30 min test. The low background and low non-specific reactivity makes the method of the present invention suitable for further application of various signal amplification techniques for antibody detection.

Furthermore, the method of the present invention provides, in one embodiment, an assay that is not species-dependent. Specifically, detection of antibodies against a specific antigen can be applied, without special modifications, for detection of antibodies in human, as well as animal sera/plasma. Moreover, the present method can, in an embodiment, detect antibody classes involved in the humoral immune response (e.g., IgG, IgM, IgA, IgE), such that analysis of the antibody class involved in specific immune complex formation with the labeled antigen can be done as a second step using appropriate secondary conjugates.

In general, the present method allows for increased sensitivity of detection of antibody classes that have more than two binding sites for antigens, for instance, IgM pentamer or IgA dimer. As such, the present method can narrow the "window period" for serological detection of infection due to more sensitive detection of IgM antibodies during the early phase of seroconversion. In addition, the present method can be valuable for detection of secretory IgA antibodies in various secretions containing the first line of humoral antimicrobial defense (e.g., saliva, intestinal, respiratory, erythema, gastrointestinal).

In another embodiment, the present method permits an application of new immune complex-forming reagents for quantitative detection of an antigen (e.g., VlsE protein). Sensitivity of better than 1 ng/ml can be attained using a version of the new test in combination with anti-C6 peptide antibody.

In certain preferred embodiments, the present invention takes advantage of the ability of all natural antibodies to bind at least two identical molecules of antigens by binding one antigen or hapten though each of the two arms of the immunoglobulin structure. In preferred embodiments the invention utilizes two basic types of peptide antigen conjugates which are recruited into a specific immune complex by the antibody to be detected. The resulting immune complex may be selectively captured on a solid phase without interference from even a large excess of non-specific immunoglobulins present in sample. The presence of a detector label on one of the two peptide antigen conjugates allows for the detection and, in certain embodiments, the quantitation of the specific immune complex, which is proportionate to the amount of specific peptide-binding antibody that is present in the test sample.

In preferred embodiments, the first peptide is conjugated directly or indirectly to a detector label by means known in the art so that the structure of the epitope recognized by the antibody is retained (for example, a selected functional group may be attached to one the terminal aminoacids). This conjugate is herein referred to as the third component or the third conjugate component of the immunoassay or of the present invention. The second peptide conjugate according to the present invention is the peptide conjugated directly or indirectly to partner of bioaffinity pair (i.e. to a ligand-binding moiety or the ligand to which it binds-preferably with a high affinity). In preferred embodiments this high affinity binding partner has a higher mol weight than its functional (affinity) counterpart. This conjugate of the peptide to the component of the bioaffinity pair is herein referred to as the second component or the second conjugate component of the immunoassay of the present invention. These conjugates should preserve functional activity of both biologically active components—i.e. of both the antigenic antibody-binding activity of the peptide as well as the binding activity of the bioaffinity partner. The third component of the system participating in specific antibody detection is a conjugate of the second component of the bioaffinity pair (i.e. a ligand where a ligand-binding moiety is incorporated into the second component and a ligand-binding moiety where a ligand is incorporated into the second component) with a macromolecular carrier which can be (or has been) immobilized on a solid phase. The invention teaches the preparation of a multiplicity of reagents of the capture system which provide efficient adsorption of reagent on various types of solid phases with high binding capacity for labeled specific immune complex. The effect of the presence of components of the bioaffinity partners in human blood (e.g. samples containing immunoglobulins where the bioaffinity partners are antibody and antigen) also has been estimated. Factors important for quantitative determinations of specific antibodies, high dose hook effect (prozoning), linearity of dependence antibody concentration-signal are also provided by the invention.

The invention provides means for optimizing the efficiency of antibody detection by determining the affinity of the antibody to be detected or measured by methods (as compared with conventional methods using solid phase immobilized peptides). In preferred embodiments, the invention includes methods that preferably include: optimization of peptide conjugates in respect of amount of peptides in each type of conjugates (as a molar ratio); optimization of the distribution of peptide between two types of conjugates; and optimization of their final concentrations in the final immunoassay. The efficacy of solid phase immunoassay is based on high local concentrations of analytes (e.g. antibodies and antigens) associated with adsorption on solid phase—which promotes the immunological antigen-antibody reaction through the law of mass action. Special approaches are known in the art for preparation of peptide antigens and their adsorption on a solid phase which increase concentration of peptides on solid phase (polymers with multiple peptides, peptides with repeating epitopic sequence ets). Frequently used approaches for peptide immobilization are based on the use of Streptavidin (StrAv) and biotinylated peptide, which theoretically permit for formation of immobilized complexes containing up to four peptides in a single immobilized complex. The Biotin/Streptavidin/Avidin/Antibiotin bioaffinity systems currently available are provide the most versatile system with various applications in area of bioanalytical and diagnostic detection system. The high affinity and specificity of biotin-streptavidin interaction, stability of StrAv, presence of four biotin-binding sites, commercial availability of reagents contribute to making this system the preferred one among bioaffinity pairs available. This system was utilized in the method of the instant invention as a preferred system for demonstrating the advantages of the invention. Typically, StrAv is used as solid-phase immobilized reagent as component for immobilization of biotin-labeled specific ligands or additional components of detection system participating in specific capture of analytes, while biotin is typically used for the labeling of specific or supplementary analytes and detector labels. In contrast, the present invention demonstrates the advantages of reversing these roles of StrAv and biotin counterparts.

The development of a test system for detection of antibodies against two peptide antigens is important for, for example, serological diagnosis of Lyme disease. The invention provides methods for the detection of different types of immune responses. For example, one antigen peptide characteristic of Lyme disease is peptide C6, representing a conservative region of one of the variable domains of VLSe of *B. burgdorferi*. C6 is known as an epitope which elicit primarily IgG response, typical seroconversion from IgM to IgG response has not been found for this peptide, although IgM components can be detected (see, e.g., Liang F. T at al. (1999) J. Clin. Microbiol. 37:3990–3996). The second peptide, C10 representing an immunogenic C-terminal epitope of OspC protein of *B. burgdorferi* is known as an epitope which results in a persistent IgM response at all stages of disease without typical IgM-IgG switching. The C10 peptide is considered to be antigen which, if detected, can improve the sensitivity and accuracy of diagnosis of early Lyme borreliosis (see Mathiesen M. J. et al. (1998) J. Clin. Microbiol. 36:3474–3479).

Both peptides C6 and C10 modified at N-terminal with biotin and immobilized on solid phase through StrAv bridge work well as antigens in conventional assays using anti-human IgG/IgM enzyme conjugates. Covalent conjugates of both peptides through N-terminal Cys with maleimide activated BSA as described in Examples also function well as reagents for immobilization on solid phase. Cross-reactive results have been found, however, for some sera samples related to the presence of antigenic substances on the solid phase not related to the specific peptide epitopes. The method of the invention provides an additional test for analysis of specificity of the immunoassay signal based on inhibition of signal using addition of an excess of non-modified pure peptide to diluted sera samples before transferring into antigen coated wells. Applied to the Lyme antigens, this approach has shown that C6 peptide can inhibit very efficiently specific signals at very low concentration, but C10 can not. This phenomenon was examined through the method of the invention by analysis of inhibitory activity of various peptide-BSA and peptide-StrAv conjugates.

In general the method of the invention provides an immunoassay which provides unique compositions, but also utilizes components and methodologies used in the art. For example, U.S. Pat. Nos. 4,778,751, 4,945,042, 5,236,849, 5,312,730, 5,705,338, 5,989,806, 6,030,770 and 6,121,006, the contents of which are incorporated by reference herein in their entirety, provide standard methodologies and reagents for use in the method of the present invention.

As used herein, a "label" is any molecule, which produces or can be induced to produce a signal. The label may be conjugated to an analyte or an antibody, or to another molecule such as a receptor or a molecule that can bind to a receptor such as a ligand, particularly a hapten. In the subject invention, the label can be a member of the signal producing system, as defined below, that includes a signal producing means.

The label may be isotopic or nonisotopic, preferably nonisotopic. By way of example and not limitation, the label can be a part of a catalytic reaction system such as enzymes, enzyme fragments, enzyme substrates, enzyme inhibitors, coenzymes, or catalysts; part of a chromogen system such as fluorophores, dyes, chemiluminescers, luminescers, or sensitizers; a dispersible particle that can be non-magnetic or magnetic, a solid support, a liposome, a ligand, a receptor, a hapten radioactive isotope, and so forth.

Enzymes, enzyme fragments, enzyme inhibitors, enzyme substrates, and other components of enzyme reaction systems can be used as labels. Where any of these components is used as a label, a chemical reaction involving one of the components is part of the signal producing system.

When enzymes are employed, molecular weights of the label typically range from about 10,000 to 600,000, more usually from about 10,000 to 300,000, and the involved reactions will be, for the most part, hydrolysis or redox reactions.

Coupled catalysts can also involve an enzyme with a non-enzymatic catalyst. The enzyme can produce a reactant, which undergoes a reaction catalyzed by the non-enzymatic catalyst or the non-enzymatic catalyst may produce a substrate (includes coenzymes) for the enzyme. A wide variety of non-enzymatic catalysts, which may be employed are found in U.S. Pat. No. 4,160,645 (1979), the appropriate portions of which are incorporated herein by reference.

The enzyme or coenzyme employed provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149, columns 19 to 23, and U.S. Pat. No. 4,318,980, columns 10 to 14, which disclosures are incorporated herein by reference.

A number of enzyme combinations are set forth in U.S. Pat. No. 4,275,149, columns 23 to 28, which combinations can find use in the subject invention. This disclosure is incorporated herein by reference.

Of particular interest are enzymes, which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference.

When a single enzyme is used as a label, such enzymes that may find use are hydrolases, transferases, lyases, isomerases, ligases or synthetases and oxidoreductases, preferably, hydrolases. Alternatively, luciferases may be used such as firefly luciferase and bacterial luciferase. Primarily, the enzymes of choice, based on the I.U.B. classification are: Class 1. oxidoreductases and Class 3. Hydrolases; particularly in Class 1, the enzymes of interest are dehydrogenases of Class 1.1, more particularly 1.1.1, 1.1.3, and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the oxidases, glucose oxidase is exemplary. Of the peroxidases, horse radish peroxidase is illustrative. Of the hydrolases, alkaline phosphatase, beta-glucosidase and lysozyme are illustrative.

Those enzymes, which employ nicotinamide adenine dinucleotide (NAD) or its phosphate (NADP) as a cofactor, particularly the former, can be used. One preferred enzyme is glucose-6-phosphate dehydrogenase, preferably, NAD-dependent glucose-6-phosphate dehydrogenase.

The label can also be fluorescent either directly or by virtue of fluorescent compounds or fluorescers bound to a particle or other molecule in conventional ways. The fluorescent labels will be bound to, or functionalized to render them capable of binding (being conjugated) to, optionally through a linking group, cyclosporin or antibodies or receptors for cyclosporin.

The fluorescers of interest will generally emit light at a wavelength above about 350 nm, usually above about 400 nm and preferably above about 450 nm. Desirably, the fluorescers have a high quantum efficiency, a large Stokes shift, and are chemically stable under the conditions of their conjugation and use. The term luminescent label is intended to include substances that emit light upon activation by electromagnetic radiation, electro chemical excitation, or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p-diaminostilbenes, pyrenes, quaternary phenanthridine salts, 9-aminoacridines, p,p'-diaminostilbenes imines, anthracenes, oxacarboxyanine, merocyanine, 3-aminoequilenin, perylene, bis-benzoxazole, bis-p-oxazolyl benzene, 1,2-benzophenazine, retinol, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates, oxides, and salts. Exemplary fluorescers are enumerated in U.S. Pat. No. 4,318,707, columns 7 and 8, the disclosure of which is incorporated herein by reference.

Energy absorbers or quenchers can be employed either separately or in conjunction with one another. The absorber or quencher can additionally be bound to a solid insoluble particle of at least about 50 nm in diameter. When the distance between the absorber and the quencher resulting from specific binding events (such as antibody-antigen binding) too small, the fluorescence of the absorber is quenched by the quencher. The quencher may be the same or different, usually different, from the fluorescer.

An alternative source of light as a detectable signal is a chemiluminescent source, and, therefore, a label can be a chemiluminescent compound. The chemiluminescent source involves a compound, which becomes electronically excited by a chemical reaction and may then emit light which serves as the detectable signal or donates energy to a fluorescent acceptor.

A diverse number of families of compounds have been found to provide chemiluminescence under a variety of conditions. One family of compounds is 2,3-dihydro-1,4-phthalazinedione. The most popular compound is luminol, which is the 5-amino analog of the above compound. Other members of the family include the 5-amino-6,7,8-trimethoxy- and the dimethylamine-[ca]benzo analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino- and para-methoxy-substituents. Chemiluminescence may also be obtained with geridinium esters, dioxetanes, and oxalates, usually oxalyl active esters, e.g., p-nitrophenyl and a peroxide, e.g., hydrogen peroxide, under basic conditions. Alternatively, luciferins may be used in conjunction with luciferase or lucigenins.

Conjugate—A conjugate is a molecule comprised of two or more subunits bound together, optionally through a linking group, to form a single structure. The binding can be made either by a direct connection (e.g. a chemical bond) between the subunits or by use of a linking group. For example, in one context of the present invention, a peptide antigen is conjugated, optionally through a linking group, a detectable label. In a second context, the peptide antigen is conjugated to a member of a high-affinity binding pair (i.e. preferably a ligand-binding moiety).

Conjugation—Conjugation is any process wherein two subunits are linked together to form a conjugate. The conjugation process can be comprised of any number of steps.

Receptor—A receptor is any compound or composition capable of recognizing a particular spatial and polar organization of a molecule. These organized areas of a molecule are referred to as epitopic or determinant sites. Illustrative naturally occurring receptors include antibodies, enzymes, fab fragments, poly(nucleic acids), complement component, i.e. thyroxine binding globulin, lectins, protein A, and the like. Receptors are also referred to as antiligands. A natural receptor exists that binds specifically to cyclosporin.

Ligand—A ligand is any organic molecule for which a receptor naturally exists or can be prepared. For example biotin is a high-affinity ligand which binds to avidin (or strepavidin).

Hapten—Haptens are capable of binding specifically to corresponding antibodies, but do not themselves act as immunogens (or antigens) for preparation of the antibodies. Antibodies which recognize a hapten can be prepared against compounds comprised of the hapten linked to an immunogenic (or antigenic) carrier. Haptens are a subset of ligands.

Member of a specific binding pair—A member of a specific binding pair (sbp member) is one of two different molecules, having an area on the surface or in a cavity, which specifically binds to and is thereby defined as complementary with a particular spatial and polar organization of the other molecule. The members of the specific binding pair are referred to as ligand and receptor (antiligand). For example, avidin and biotin form a preferred specific binding pair. The specific binding pair may also be members of an immunological pair such as antigen-antibody, although other specific binding pairs, such as biotin-avidin, hormones-hormone receptors, nucleic acid duplexes, IgG-protein A, DNA-DNA, DNA-RNA, and the like, are not immunological pairs but are specific binding pairs.

A solid phase (or support or surface)—A solid phase is a porous or non-porous water insoluble material. The solid phase can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed. Other materials, which can be employed, are described above in the definition of immunogenic carrier particles and below in the definition of a signal producing system. Other preferred solid phase membrane materials are described below in the examples.

The binding of members to the support or surface may be accomplished by well-known techniques, commonly available in the literature, and described above in the definition of immunogenic carrier particles. The surface can have any one of a number of shapes, such as strip, rod, particle, including bead, and the like. The surface will usually be polyfunctional or be capable of being polyfunctionalized or be capable of binding an sbp member through specific or non-specific covalent or non-covalent interactions. A wide variety of functional groups for linking are described in the definition of immunogenic carrier particles.

The length of a linking group or chemical linker" to the peptide antigen or ligand may vary widely, depending upon the nature of the compound being linked, the effect of the distance between the compound being linked and the support on the assay and the like.

Signal producing system—The function of the signal producing system is to produce a product, which provides a detectable signal related to the amount of bound and/or unbound label. The signal producing system may have one or more components, at least one component being a label. The signal producing system includes all of the reagents required to produce a measurable signal including signal producing means capable of interacting with the label to produce a signal. The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes, which absorb light in the ultraviolet or visible region, phosphors, or fluorescers.

The signal producing means is capable of interacting with the label to produce a detectable signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to other molecules or to a support.

The signal producing system including the label can include one or more particles, which are insoluble particles of at least about 50 nm and not more than about 50 microns, usually at least about 100 nm and less than about 25 microns, preferably from about 0.2 to 5 microns, diameter. The particle may be organic or inorganic, porous or non-porous, preferably of a density approximating water, generally from about 0.7 to about 1.5 g/mL, and composed of material that can be transparent, partially transparent, or opaque. Generally, particles utilized as a label will have similar characteristics to those described above in the definitions of an immunogenic carrier and a support or surface.

Many different types of particles may be employed for modulating light emission. Of particular interest are carbon particles, such as charcoal, lamp black, graphite, colloidal carbon and the like. Besides carbon particles metal sols may also find use, particularly of the noble metals, gold, silver, and platinum. Other metal-derived particles may include metal sulfides, such as lead, silver, or copper sulfides or metal oxides, such as iron or copper oxide.

Fluoresceinated latex particles are taught in U.S. Pat. No. 3,853,987 and are available commercially as Covaspheres from Covalent Technology Corp.

Quantitative, semiquantitative, and qualitative methods as well as all other methods for determining antibody or antigen are considered to be methods of detecting the antibody or antigen. For example, a method that merely detects the presence or absence of an antibody in a sample suspected of containing the antibody is considered to be included within the scope of the present invention.

Synonyms for the phrase "measuring the amount of antibody", which are contemplated within the scope of the present invention include, but are not limited to, detecting, measuring, or determining antibody; detecting, measuring, or determining the presence of antibody; and detecting, or determining the amount of antibody. The same principle applies to the phrase "measuring the amount of antigen".

An "antibody sample" is a sample suspected of containing an antibody—i.e. any sample, which is reasonably suspected of containing an antibody, can be analyzed by the method of the present invention. Such samples can include human, animal, or man-made samples. The sample can be prepared in any convenient medium, which does not interfere with the assay. Typically, the sample is an aqueous solution or a natural fluid, preferably, urine, whole blood, serum, plasma, or saliva more preferably, whole blood.

In the methods of the invention the antibody to be detected is a specific immunoglobulin, preferably a specific IgA, IgD, IgE, IgG, IgM, and subclasses thereof, and more preferably a specific IgE, or a class of antibodies, such as immunoglobulins, preferably selected from the group consisting of total IgA, total Igd, total IgE, total IgG, total IgM and isotypes thereof, most prefer ably total IgE.

The ligand antigen, antibody or hapten bound to biotin can be any immunologically active substance, such as an allergen, antibodies, such as polyclonal antibodies, monoclonal antibodies including recombinant antibodies or fragmented antibodies, preferably an allergen and/or a polyclonal anti-immunoglobulin, such as goat anti-human polyclonal serum supplied by Ventrex Laboratories, Inc., Portland, Me., Catalog No. 77660. In the reference immunoassay said antibody is preferably directed against the constant portion of the class of antibodies to be measured, i.e. an antibody directed against the IgE-antibodies.

By biological fluid is meant any clinical sample, such as blood, plasma, serum, urine or saliva, which also includes any biological fluid which is excreted, secreted or transported internally in an organism.

EXAMPLE

The following detailed guidance and examples are provided to further illustrate and define preferred aspects of the invention.

Detecting Anti-Lyme Disease Antibodies

Affinity-purified anti-peptide antibodies were isolated (Example 6) from two different patient sera pools—one from patients with late Lyme disease, which contained only IgG antibodies against the C6 peptide, and the second from patients at early stage of Lyme disease containing both IgG and IgM classes of antibodies against C6 and C10 peptides. Affinity purification was conducted according to conventional ELISA test with solid-phase immobilized peptides (see Example 13). A series of C6-BSA, C10-BSA, C6-StrAv and C10-StrAv conjugates at various ratios of peptide/BSA (from 1:1 to 8:1) have been synthesized and tested for inhibitory activity for IgG and IgM antibodies in preparations of affinity purified anti C6 and anti-C10 antibodies (see Examples 7 and 14). Table 1 below illustrates the differences in inhibitory activity (which reflects affinity) seen with non-conjugated peptides and with peptides having various molar ratios of peptide/BSA as well as the source of the antibody—i.e. early or late stage of disease.

TABLE 1

Concentrations of non-conjugated peptides and peptide-BSA conjugates which induce 50% inhibition of binding of anti-peptide antibodies with solid-phase immobilized peptides

|  | Anti-C6 IgG High affinity | Anti-C6 IgG Low affinity | Anti-C6 IgM Low affinity |
|---|---|---|---|
| C6 non-conjugated | 1–1.5 ng/ml | 10–15 ng/ml | 5–8 ug/ml |
| C6-BSA 1:1 | 0.6–0.8 ng/ml | 5–10 ng/ml | 10–20 ng/ml |
| C6-BSA 2:1 | 0.6–0.8 ng/ml | 1.5–2.0 ng/ml | 5–10 ng/ml |
| C6-BSA 4:1 | 0.6–0.8 ng/ml | 0.8–1.0 ng/ml | 2–4 ng/ml |
| C6-BSA 8:1 | 0.6–0.8 ng/ml | 0.4–0.6 ng/ml | 1–2 ng/ml |

|  | Anti-C10 IgG Low affinity | Anti-C10 IgM Low affinity |
|---|---|---|
| C10 non-conjugated | 50–80 ug/ml | 80–100 ug/ml |
| C10-BSA 1:1 | 3–4 ug/ml | 3–4 ug/ml |
| C10-BSA 2:1 | 1.5–2.0 ug/ml | 1–2 ug/ml |
| C10-BSA 4:1 | 0.6–1.0 ug/ml | 1–2 ug/ml |
| C10-BSA 8:1 | 0.1–0.2 ug/ml | 30–60 ng/ml |

The binding of anti-C6 IgG antibodies isolated from late serum with solid-phase immobilized peptide inhibited with almost equal efficiency to non-conjugated C6 peptide and all C6-BSA conjugates. For anti-C6 antibodies isolated from serum of patient at early stage of Lyme disease inhibitory activity (affinity) of non-conjugated C6 peptide and C6-BSA conjugates differ significantly. There was a direct relationship between the amount of peptide in BSA conjugates and its activity as an inhibitors of IgG and IgM anti-C6 antibody activity in solution. Even more significant is the difference between non-conjugated peptide and BSA-C10 conjugates in inhibition of IgG and IgM anti-C10 antibodies. Almost three order of magnitude difference between the concentration of non-conjugated C10 and C10-BSA 8:1 conjugate was required to reduce the binding of anti-C10 antibodies by 50% in solution with solid-phase immobilized peptide. These results demonstrate that, optimally, more than one peptide should be present in peptide conjugates to optimize binding in solution with specific anti-peptide antibodies having low affinity to peptide epitopes.

Figure 1:
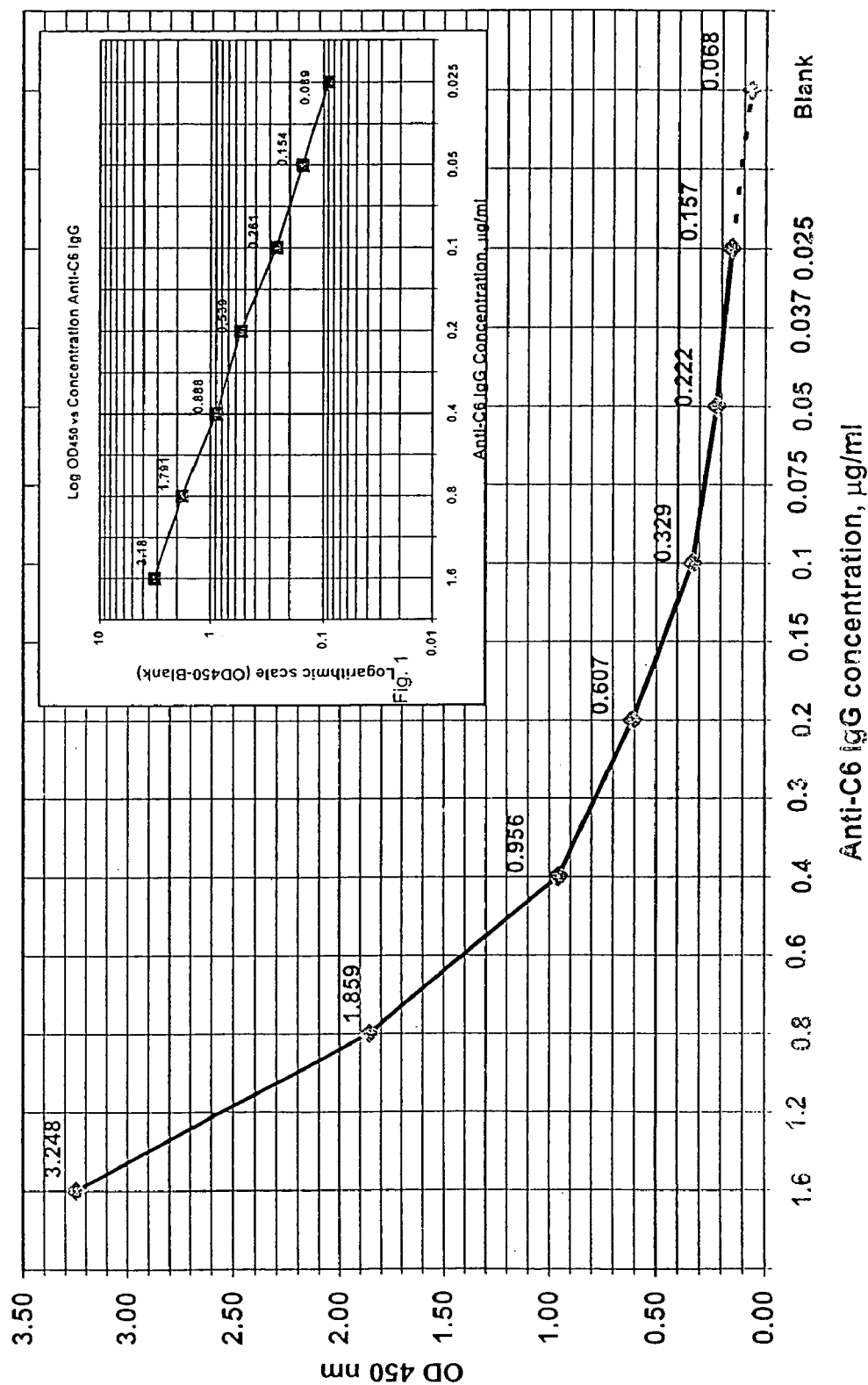
FIG. 1 shows a calibration curve for detection of high affinity anti-C6 IgG antibodies added to normal human serum.
Figure 2:
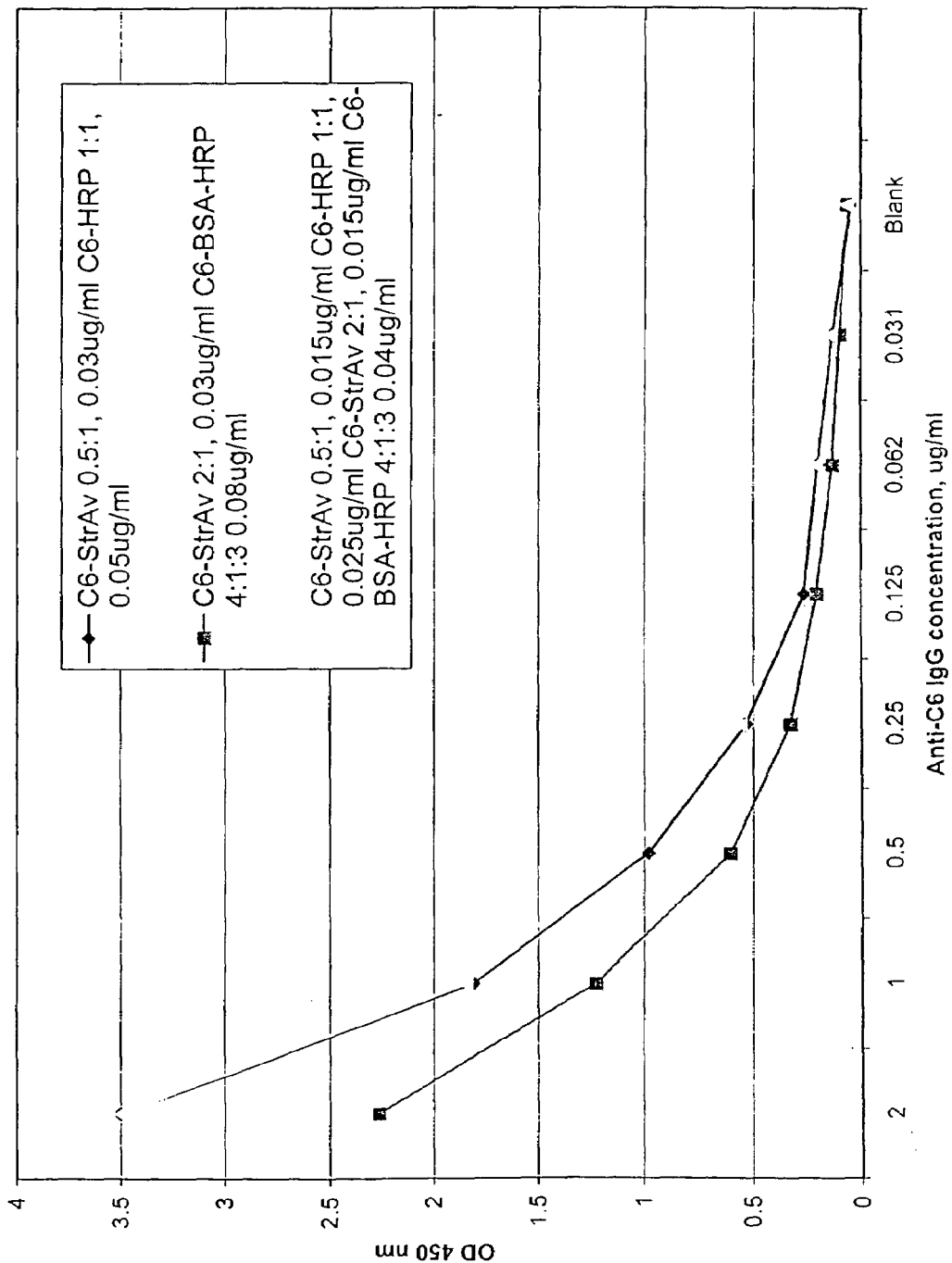
FIG. 2 shows that conjugates C6-StrAv, 2:1 and C6-BSA-HRP, 4:1:3 are less active in the detection of a high affinity antibody
Figure 3:
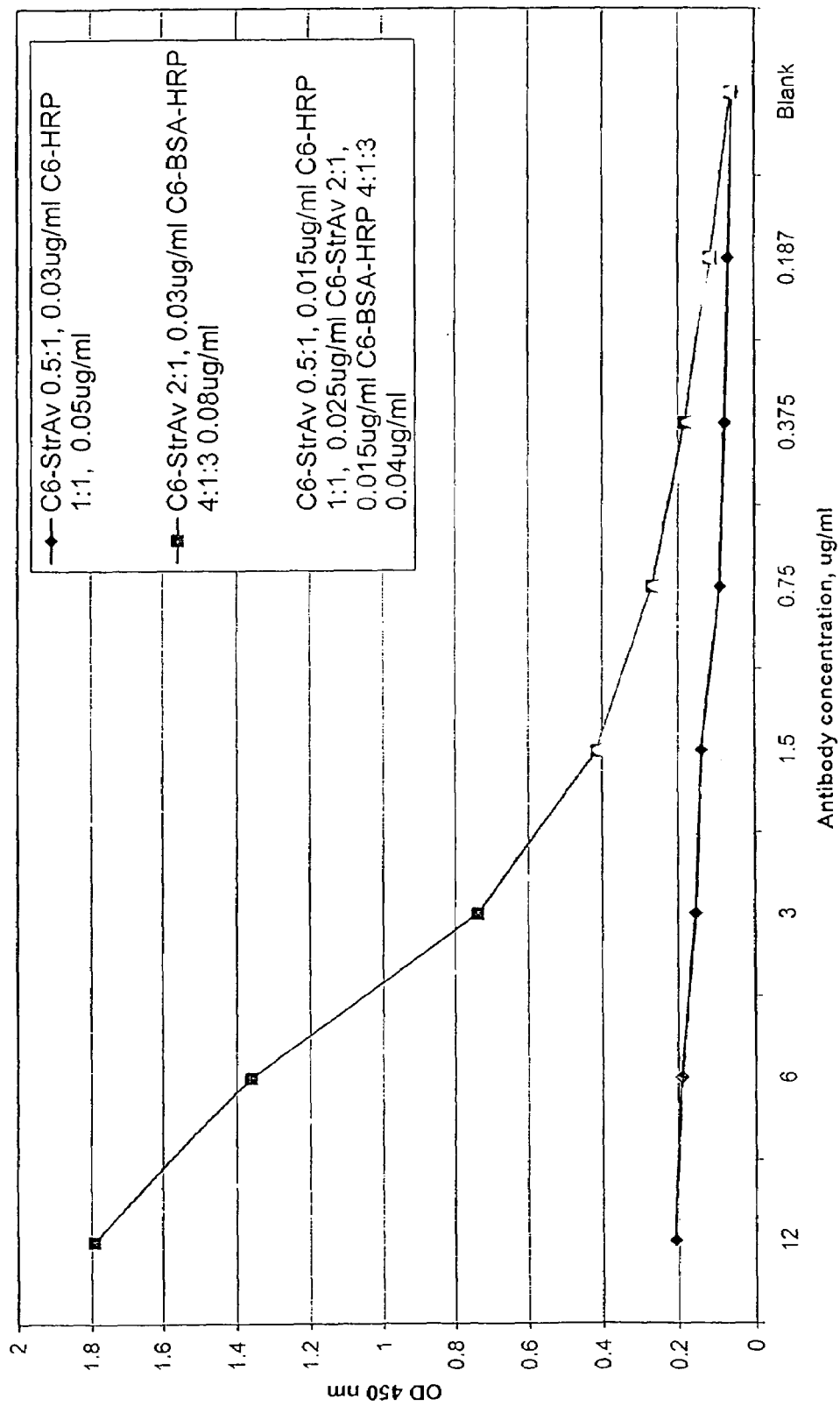
FIG. 3 shows the concentration/OD curves for detection of low affinity anti-C6 antibodies containing both IgG and IgM using various conjugates mixtures. The results shows that conjugates with one or less molecules of C6 peptide per StrAv and HRP, which detects high affinity anti-C6 antibodies with high sensitivity, fail to detect low affinity antibodies. Conjugates containing 2 or 4 molecules C6 peptide per one molecule of StrAv/BSA detect antibody with relatively good sensitivity. Mixture of all four conjugates also have similar sensitivity in detection of low affinity antibody.
Figure 4:
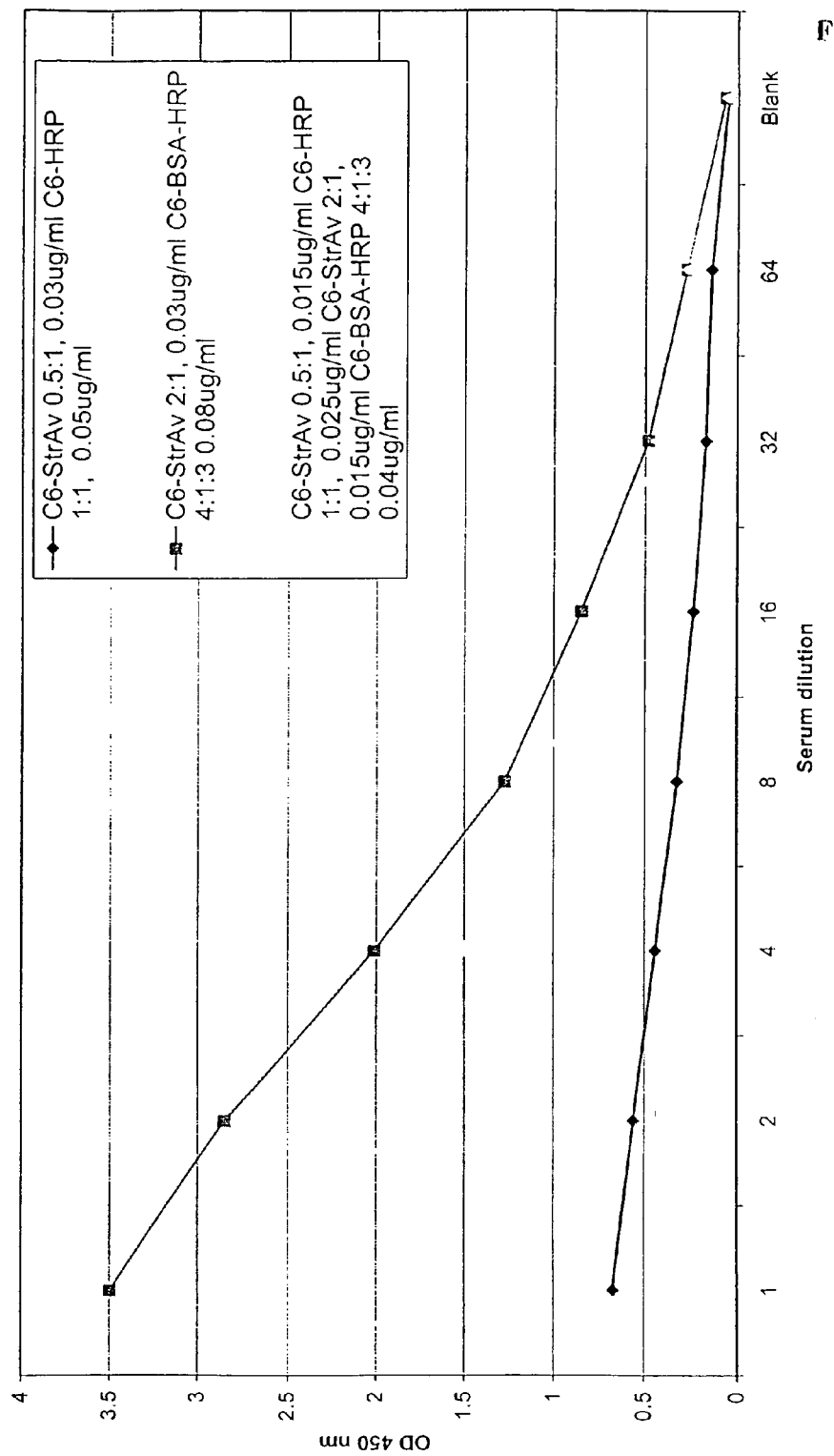
FIG. 4 shows the detection of antibodies in patient sample at an early stage of Lyme disease. A combination of peptide conjugates with various molar ratios of peptide/StrAv/HRP provided good sensitivity.
Figure 5:
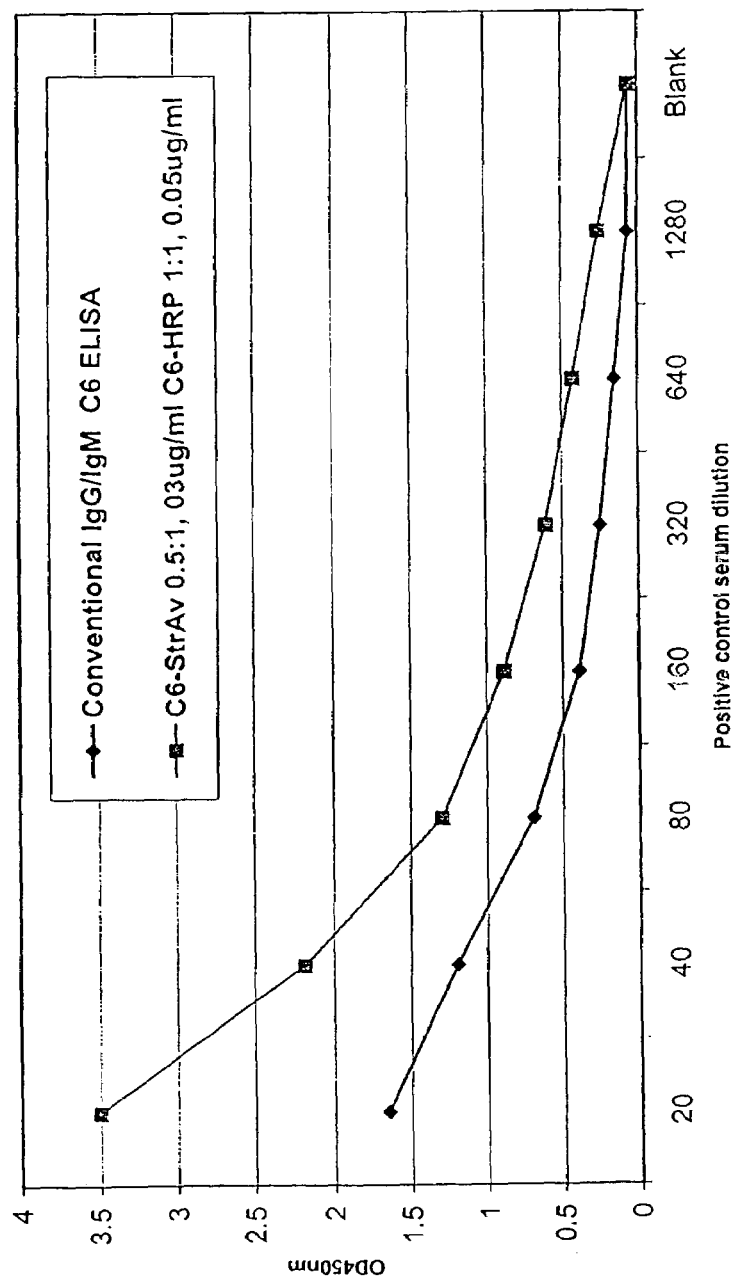
FIG. 5 shows a comparison of sensitivity of antibody detection using a conventional IgG/IgM C6 ELISA test with the assay of current invention. Positive control serum from a C6 ELISA kit, containing patient sera with anti-C6 IgG was used as source of antibodies.

In contrast, for the formation of complexes with high affinity antibodies one peptide in the peptide conjugate may be enough (FIG. 1). Conjugates of C6 and C10 peptides with detector label (HRP) were prepared two ways. First, conjugates containing 1 or less molecules of peptide per HRP molecule were prepared by direct reaction of Cys-peptides with maleimide activated HRP (see Examples 7 and 8). HRP does not have enough amino groups to introduce more maleimide groups conveniently. Conjugates of peptide-HRP with more than one peptide were prepared by conjugation of peptide-BSA conjugates having reactive maleimide groups with thyolated HRP, prepared as described in Example 4. The presence of approximately one SH groups in HRP in this case favors formation of conjugates without cross-linking problem. Conjugates containing up to 4.5 HRP molecules per one peptide_BSA-maleimide were prepared (Example 8).

As a major component of solid phase capture system the current invention describes biotinylated BSA where biotin is attached to BSA through a PEG spacer with MW3500 (Example 5). Biotechnical and biomedical application of PEG is known in the art [see, e.g., Poly(ethylene glycol) chemistry Ed by J. M. Harris, Plenum Press, New York, 1992]. The characteristics of PEG which favor its use as a spacer or linker for use in the present invention include its: hydrophilic characteristics, absence of charge, flexibility, stabilizing effect on proteins, and reduction of immunogenic properties of proteins. Accordingly, Bi-PEG-BSA is versatile reagent for adsorption on various solid phases, polystirol plates, NC and other membranes in this invention (in which high binding capacity to biotin-binding proteins and reduced non-specific adsorption effect are optimal). Bi-PEG-BSA provides enhanced affinity to the solid phase, stable adsorption, and can be applied at a concentration which may be enough for simultaneously efficient blocking of the solid phase, thereby eliminating requirement for secondary blocking reagents. As a result, the procedure for preparation of coated devices become very simple and inexpensive.

In one of embodiments of this invention the application of PEG-modified streptavidin is described in the examples which follow. The PEG-modified streptavidin may be used to enhance adsorption on various solid phases with reduced NSB reactions. StrAv, modified through amino groups with PNC activated StrAv MW 5000 has enhanced and stable adsorption on polystirol plates and NC membranes, non-specific adsorption of immunoglobulins from sera samples was also reduced and potential immunogenic epitopes on streptavidin also appear to be sheltered. Another application of PEG-modified StrAv, where effect of modification is very pronounced is adsorption on colloidal gold particles. PEG-StrAv contrary to non-modified StrAv adsorbs on colloidal particles at neutral pH at lower protecting concentration with formation stable and more active conjugates than colloidal gold conjugates prepared by adsorption of native streptavidin at optimal pH.

An important advantage of a method with dual labeled antigen is reduction of the nonspecific reactions and some cross-reactive reactions, which can contribute to false—positive results in conventional tests. The application of new peptides conjugates for analysis of a big population of normal sera samples have shown that OD values in new test are significantly lower than for the same population tested in conventional ELISA tests. For most sera tested as undiluted samples OD values were equal to the blank reagent. Low cutoff values can be calculated for new tests using various approaches, demonstrating that dual labeled antigen method better discriminate positive and negative results (see FIG. 12)

Figure 6:
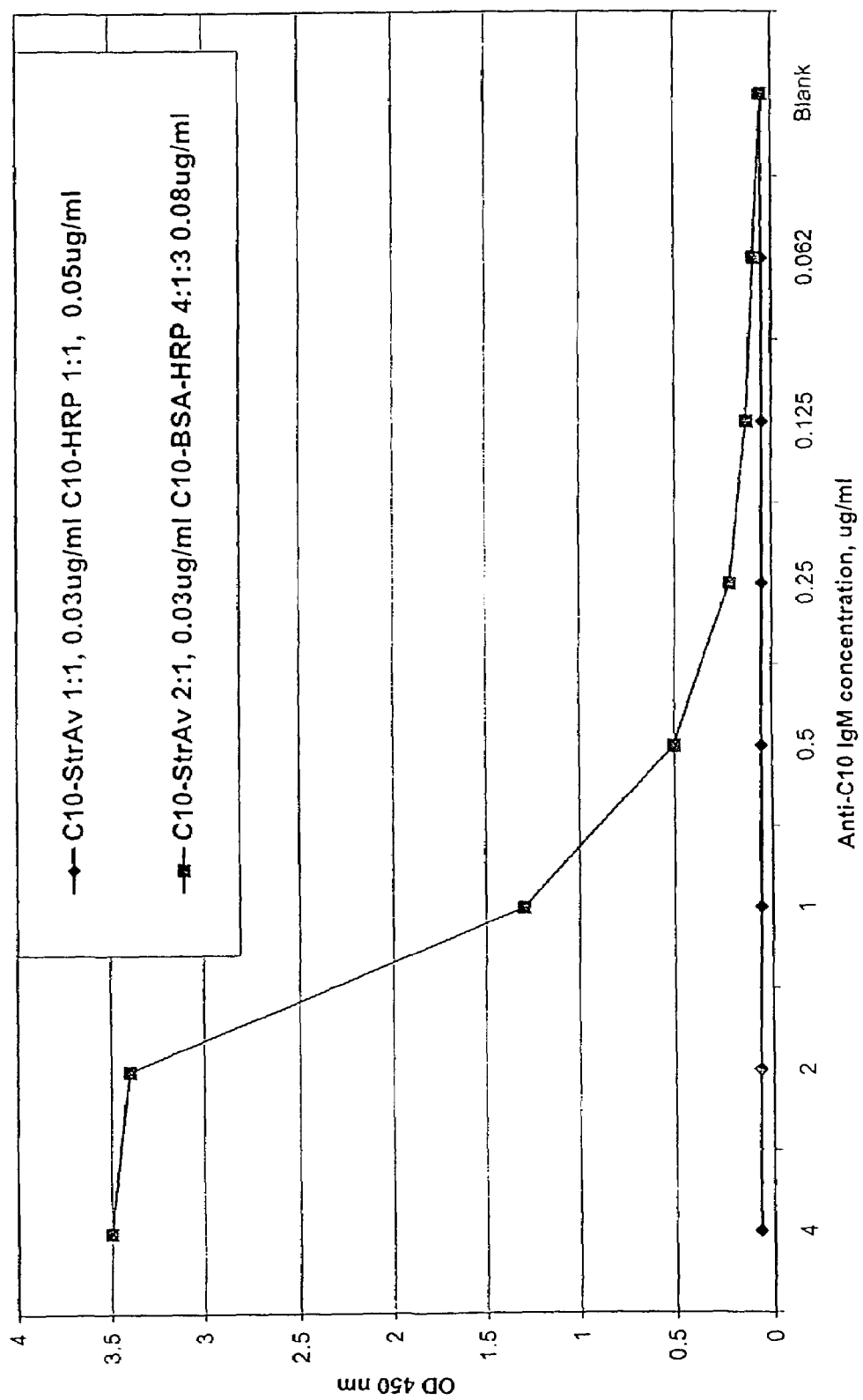
FIG. 6 shows the critical dependence of sensitivity for detection of anti-C10 low affinity IgM antibodies from amount of peptide in conjugates.
Figure 7:
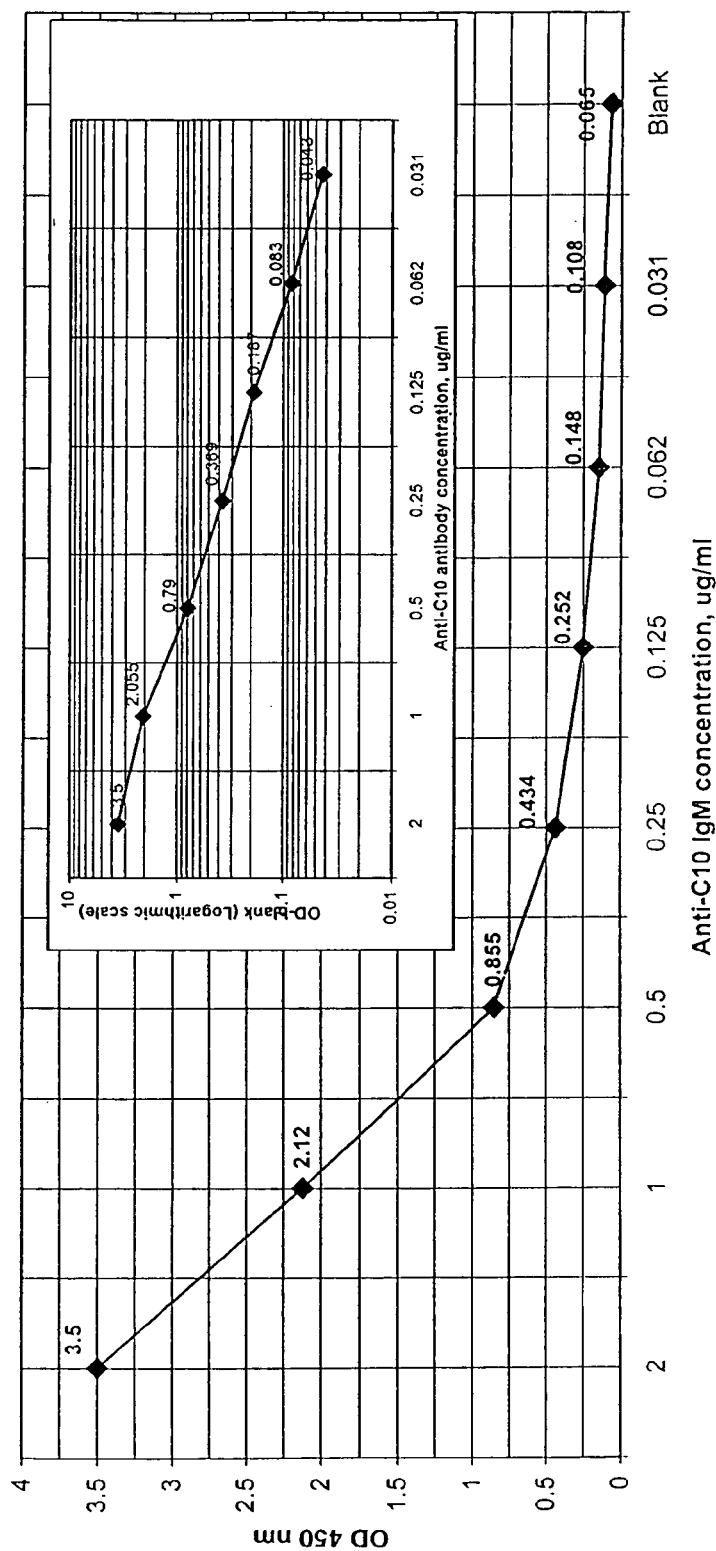
FIG. 7 shows a calibration curve and assay for linearity of detection of anti-C10 antibodies using affinity antibody from patient with early stage of infection as a calibrator. The conjugates used were C10-StrAv 2:1, 0.03 ug/ml, C10-BSA-HRP 4:1:3 0.08 ug/ml.

The formation of triple complex of anti-peptide antibody with two different peptide conjugates depends on several factors including antibody affinity, antibody class, concentration and the amount of peptide in the conjugates as well as the molar ratio of peptides and antibodies in the sample. To initiate specific complex formation in solution the two conjugates sample should be mixed to obtain a solution containing both conjugates. Several reaction products will be formed including: first, a complex of antibodies with peptide-detector label (complex 1), second, a complex of antibody with peptide conjugates of the second component of the bioaffinity pair (complex 2), and, finally, a triple complex of antibody with the two different peptide conjugates (complex 3). Complex 1 contains label, but can not be captured on solid phase, while complex 2 can be captured but does not contains label and can not detected after washing. Only triple complex 3 can be captured and detected. Antibody with only two antigen-combining sites (IgG, IgE) can be captured and detected only in complex with equal amount of both conjugates. Complexes of antibodies having four or more antigen-combining sites can be captured and detected at any ratio of conjugates in complex allowed by antibody structure at the condition that at least one of each should be present in the complex. For, example, antibodies of the IgM class containing up to 10 antigen-combining sites conditions which allow for complex formation with one molecule of peptide conjugate needed for capture and several of the peptide conjugates with label will provide for higher sensitivity of antibody detection because more label will present per each antibody in captured complex (see FIG. 6). This is only simple schematic picture.

Figure 10:
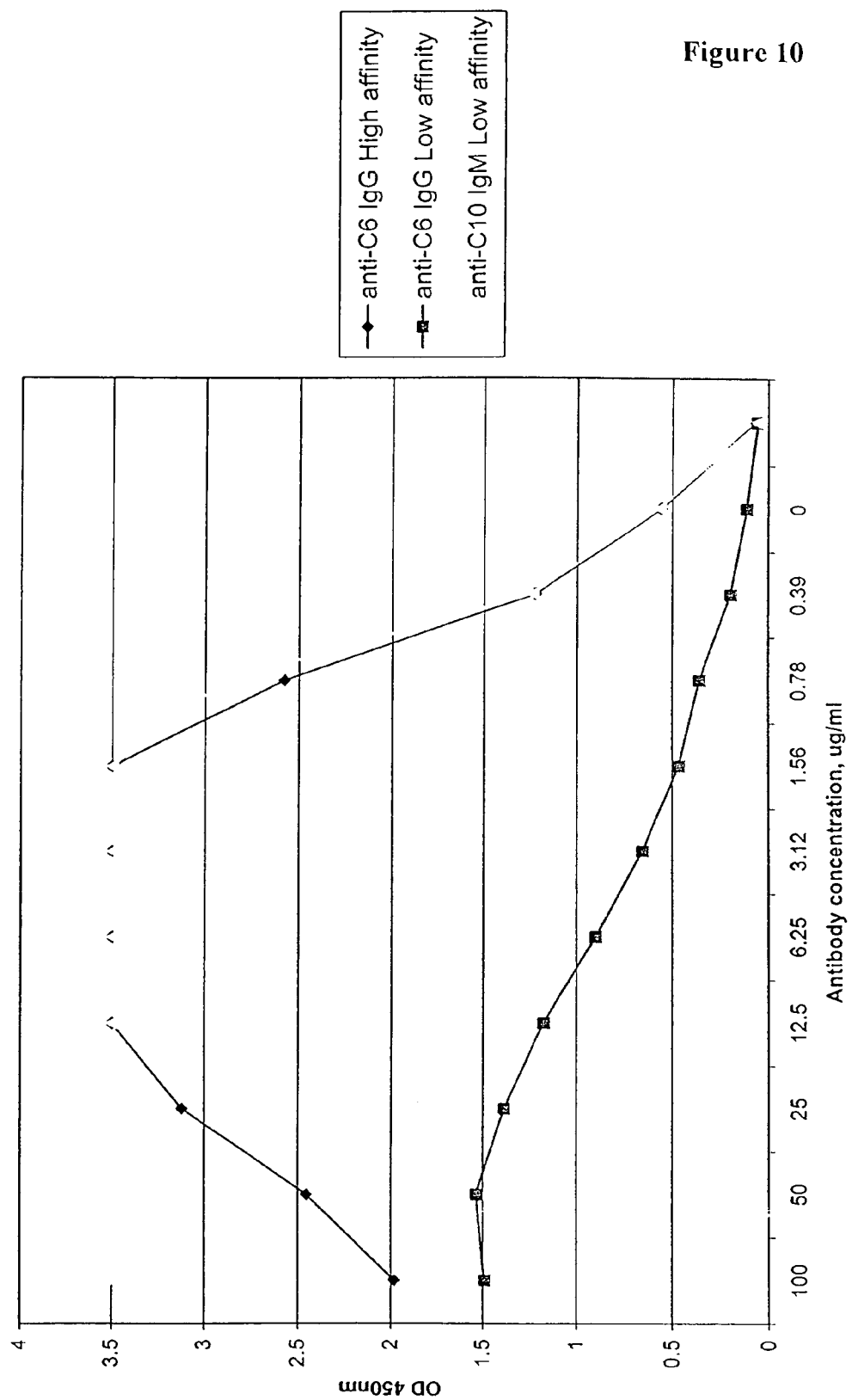
FIG. 10 shows the dependence of antibody concentration on OD over a wide range of antibody concentrations (anti-C6 high affinity, anti-C6 low affinity and anti-C10 IgM). A high dose hook effect was found only for the detection of high affinity anti-C6 IgG and observable (OD drops below OVER in ELISA reader with upper limit 3.5) at high antibody concentration exceeding range of linear response almost 10 times. Low affinity anti-C6 IgG/IgM and anti-10 IgM does not show a hook effect, which can be recognized in assay conditions at concentration of up to 100 ug/ml.
Figure 11:
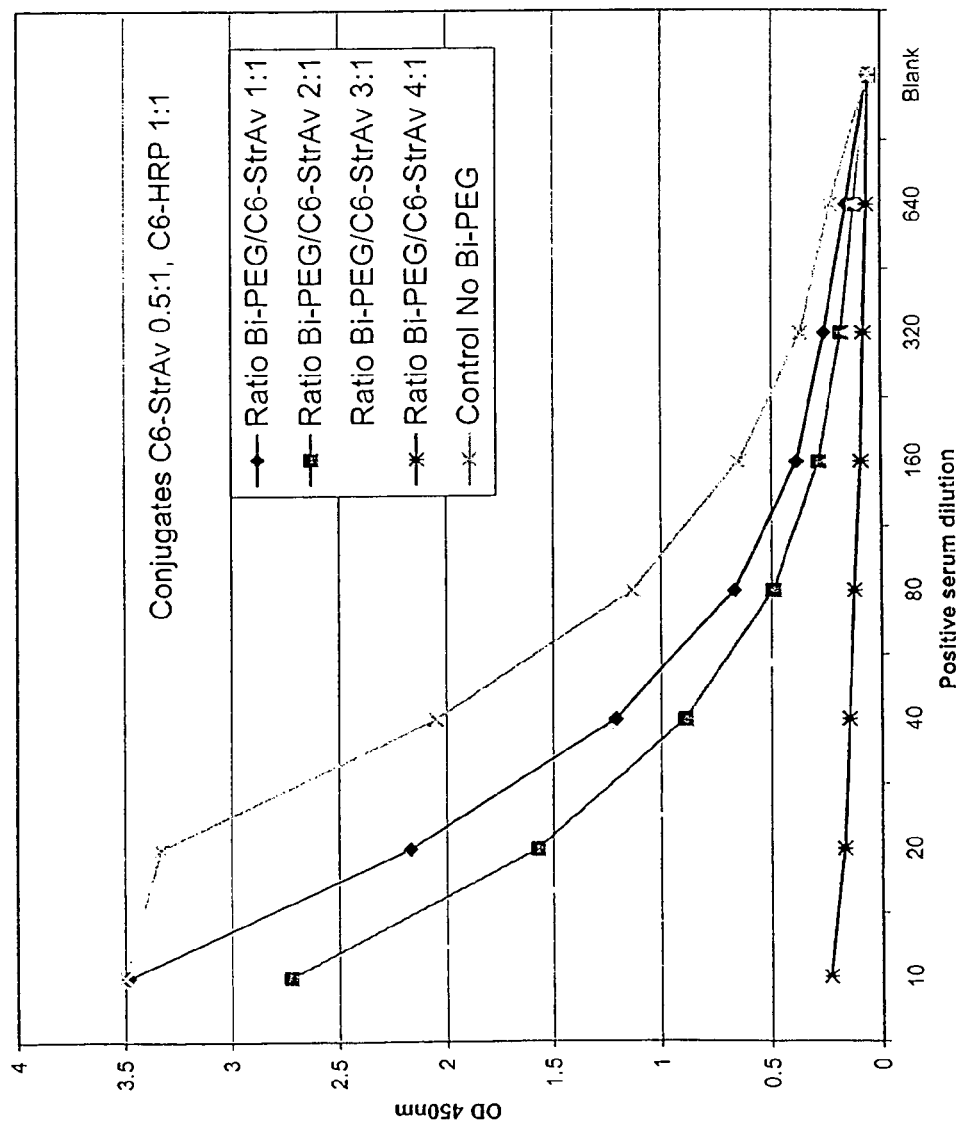
FIG. 11 shows the effect of titration of biotin-binding sites in C6-StrAv conjugates with Bi-PEG on assay sensitivity. Blocking of one binding site dos not significantly change the analytical sensitivity. The presence of only one to four biotin-binding sites was sufficient to maintain activity peptide-StrAv conjugates in the test.

Other combinations of dually-labeled antigens with antibodies are also possible-especially for conjugates containing more than one antigen molecule, when more than one antibody can be involved in complex with one polyepitopic (multiantigenic) conjugate. According to this scheme the likelihood (statistical probability) of formation of a triple immune complex is higher when total antigen concentration (amount) exceed the amount of specific antibodies—i.e. the method of the invention is particularly well suited for antibody detection in low titer samples. When antibody concentration in the antibody sample increases at a constant concentration of antigen in the conjugates, the relative ratio of complex of one type of conjugate/triple immune complex (portion of complexes with only one conjugates) increases—which can lead at appropriate ratios to formation of small amounts of triple complex and as a result to a decrease in the signal for samples with high concentration of antibodies (high dose hook effect). Using affinity purified anti-peptide antibodies spiked into normal human serum, it was found that high dose hook effect can be observed for high affinity antibodies at concentrations which significantly exceed concentration in the linear range for OD/concentration (see FIG. 10). This effect can not lead to false negative results, because it is observed at concentrations rarely present in patient samples and signals do not drops to very low levels. The sensitivity of antibody detection depends on the ratio between capture capacity of the solid phase in respect to the bioaffinity partner and the concentration of conjugate of antigen with the affinity counterpart. If the binding capacity of the solid phase with immobilized affinity partner is significantly less than the amount of conjugated counterpart in the sample, then reduction of sensitivity may arise as result of competition between conjugates not involved in immune complex formation and involved in triple or dual immune complex. Decreasing the conjugate concentration can minimize this effect, but at the same time sensitivity may drop as a result of the lowering of concentration of reagents with a concomitant reduction of antibody concentration range which can tolerate the high dose hook effect. Accordingly, by these considerations, a solid phase which can except large amounts of capture reagent, exceeding the amount of reagents in solution and not a limiting factor for selection of conjugate concentration, can provide for the highest levels of sensitivity.

Various membrane formats including dot-blot, flow-through and lateral flow formats which use membranes with high binding capacity are potentially good formats for application of the method of the current invention. Several membrane formats were developed for antibody detection using Bi-PEG-BSA as a capture reagent and peptide-StrAv, peptide-HRP and peptide-colloidal gold conjugates to demonstrate the advantages of dual labeled antigen method (see Examples 10, 11, 15, 16, 17, 18). Both membrane tests using HRP as a detector label, dot-blot (Example 17) and flow-through (Example 15) have shown analytical sensitivity exceeding the sensitivity of conventional IgG/IgM ELISA (Example 13) according to a comparison of detection limits for serially diluted positive sera. Membrane versions with colloidal gold conjugates (see Examples 16 and 17) also work well and clearly discriminate negative and positive sera. Colloidal gold conjugates of C6 peptide with C6-StrAv were also applied in lateral flow format as dry reagents in conjugate pad and Bi-PEG-BSA striped on membrane as capture line. Clear discrimination between negative and positive sera have been found.

Figure 9:
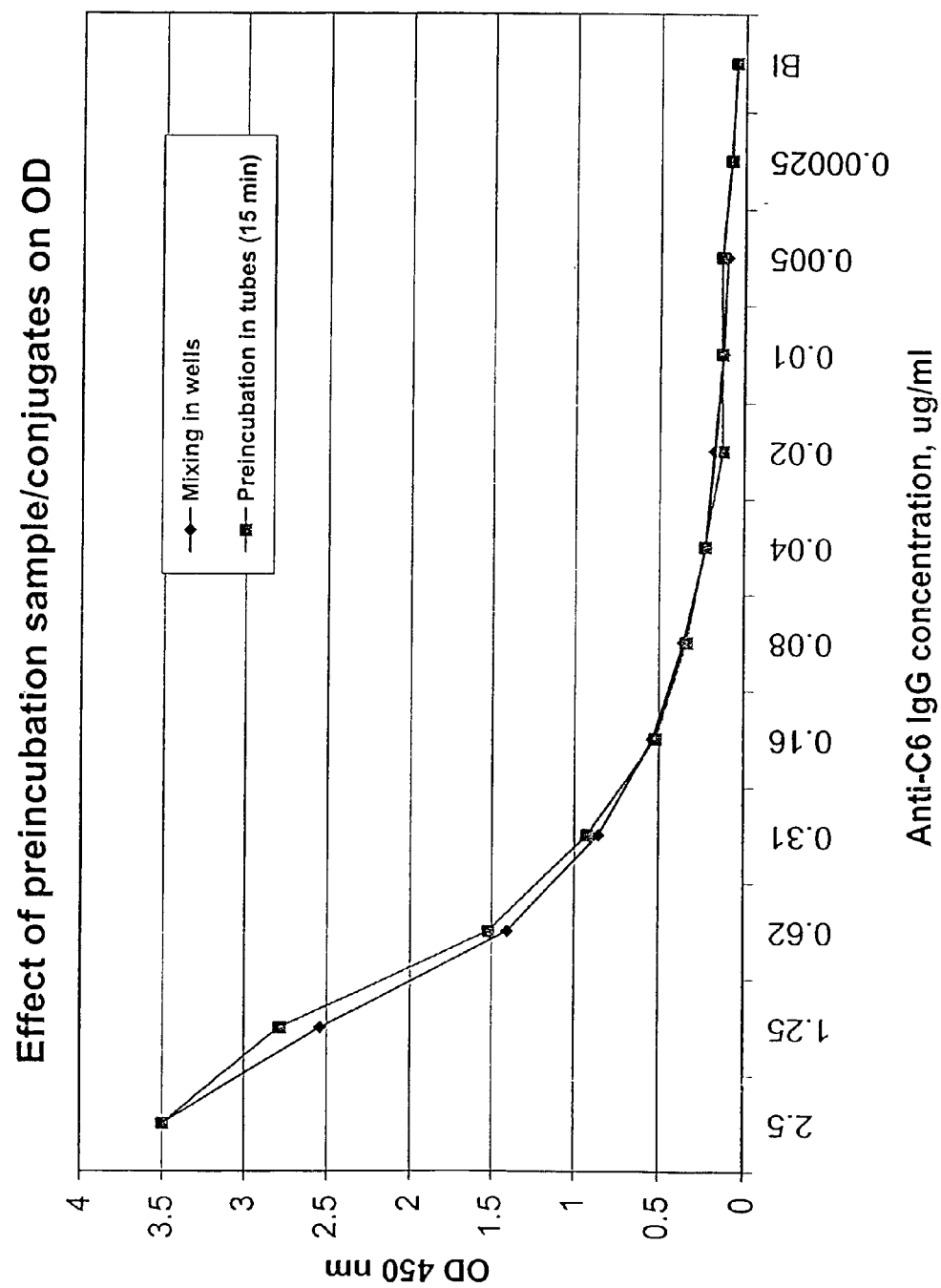
FIG. 9 shows a comparison of two means for running the assay—i.e. with the sample mixed with conjugates in a separate tube, incubated for 10 min than transferred into wells with capture reagent and with the sample mixed with conjugates directly into wells with capture reagent. Conjugates were C6-StrAv 0.5:1, 0.03 ug/ml C6-HRP 1:1, 0.05 ug/ml.

The method of the current invention accepts that formation of the immune complex with dual-labeled antigens and its capture can proceed as a single step when samples containing antibody are mixed directly with conjugates in coated solid phase. This then requires a single washing step after incubation. The process of specific complex formation and its capture can also be carried out in two steps. In this case, the sample is first incubated with conjugates and subsequently transferred into solid phase with capture reagent (see FIG. 9). Simultaneous incubation of the sample with peptide conjugates and a single washing step was especially advantageous in various tests using plates, tubes, and balls as a solid phase. Significant simplification and shortening of assay procedures for antibody detection can be achieved. As a further optimization of assay procedure, agitation may be used for acceleration of a capture process that further shortens the assay time and improves linearity of the dependence of signal/antibody concentrations. In membrane based tests, preincubation of sample with conjugates can be the procedure of choice. In rapid lateral flow tests, conjugates can be used as one reagent dried on one conjugate pad material or two antigen conjugates can be distributed among two separate conjugate pads. The formation of a specific immune complex in this last cases will precede by binding on capture line or membrane area with the applied capture reagent.

Figure 8:
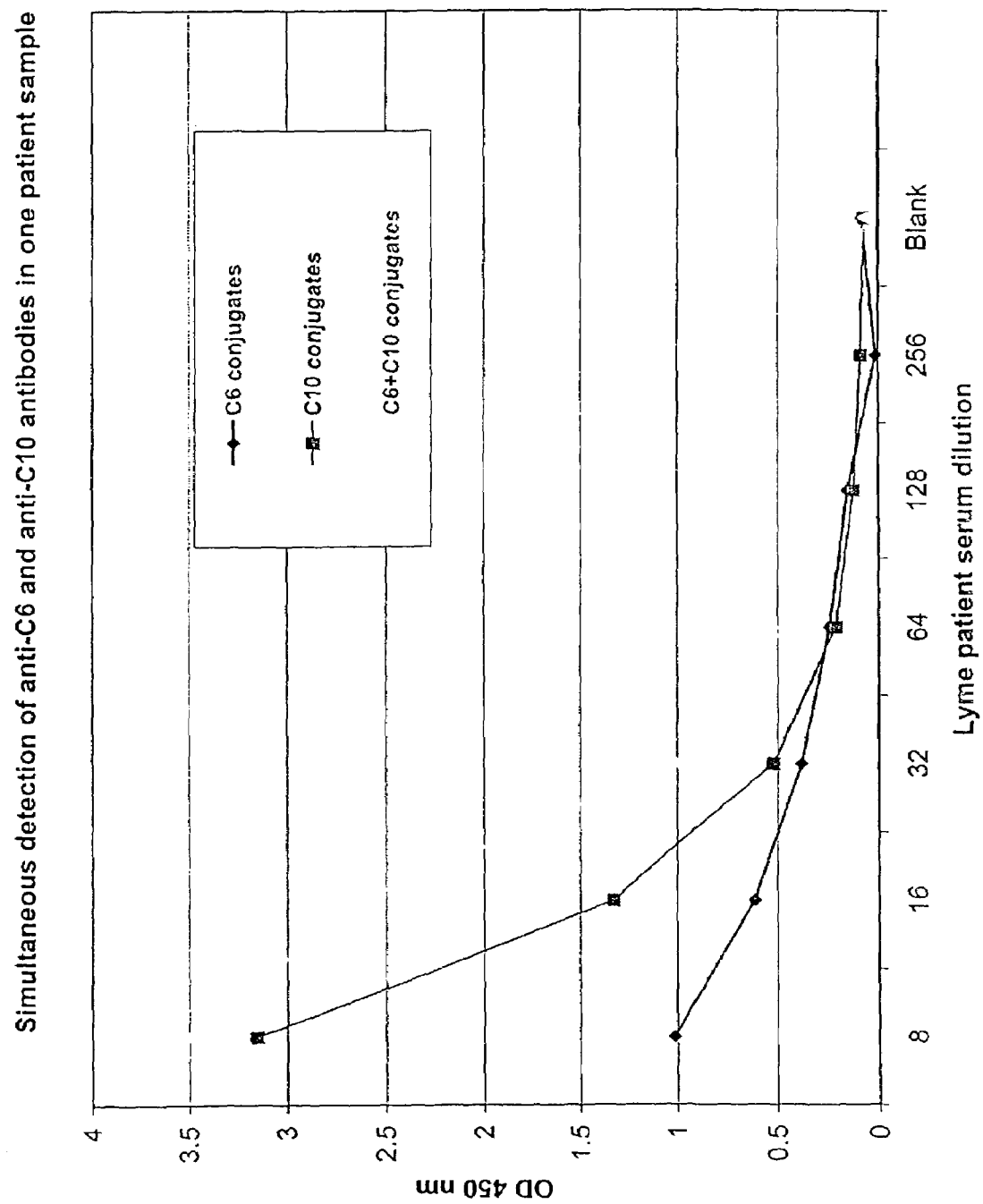
FIG. 8 shows the sensitivity for detection of anti-C6 and anti-C10 antibodies in a serum sample at separate detection using mixtures of conjugates for separate detection (C6-StrAv 0.5:1, C6-StrAv 2:1, C6-StrAv 2:1, C6-BSA-HRP 4:1:3) and (C10-StrAv 2:1, C10-BSA-HRP 4:1:3) and mixture containing all conjugates for detection both antibodies in one well.

One of the embodiments of the current invention utilizes peptide (antigen) conjugates containing more than one peptide or polypeptide (antigen type) in the conjugate with detector label and bioaffinity partner. Conjugates containing various antigens can be also mixed and used as single reagent for detection of several antibodies in a single sample (see FIG. 8). When necessary, multiple antibody classes involved in specific immune complex can be analyzed by adding a step of incubation with class-specific antibody into solid phase containing captured immune complex with dual labeled antigens as described in Example 20. Repeating this with detection antibodies specific to all the various antibody classes provides a detailed picture of the immune status of antibody production in a patient antibody sample.

Reagents and assay principles developed in current invention can also be applied for the detection of components of infectious agents bearing epitopes used for antibody detection i.e. for antigen detection. In this case (Example 19), sample, containing the antigen is first incubated with a small amount of epitope-specific antibody (this may be affinity purified using anti-peptide antibody or whole sera containing peptide-specific antibody), then the mixture is contacted with the solid phase containing the capture reagent and peptide conjugate components described above. The epitope-bearing substance in the sample competes with the peptide conjugates for antibody binding and reduces the signal in concentration dependent manner. Standard curves may be generated using known quantities of the epitope bearing substance (i.e. peptide or polypeptide or protein bearing the antigen). FIG. 14 shows examples of detection of whole recombinant VLSe protein using this approach—which demonstrates that ng amount of antigenic substance can be readily detected.

The following Examples and accompanying drawings are given for the purpose of illustrating the present invention.

C6 and C10 Peptides, Sequences and Synthesis Procedure

Peptides C6 (26 AA) and C10 (12AA) were synthesized by automatic solid phase synthesis with the fluor-etylmetoxycarbonyl (Fmoc) strategy, followed by purification by HPLC and sequence verification by mass spectroscopy. Purity of peptides was >90%. N-terminal Cys was included into both peptides and biotin also was included into N-terminal Cys of C10 peptide during synthesis. C10 peptide also contains serine residue between N-terminal Cys and a sequence of ten aminoacids corresponding to C-terminal fragment of OspC. Biotinylated C6 peptide was prepared from pure Cys-C6 by modification with Biotin-PEG-Maleimid MW 3500 (Shearwater Polymers, Inc) at equimolar ratio Cys and Maleimide in 0.1M sodium phosphate buffer, pH 7.0. The structure and immunogenic properties of both peptides are well known in the art.

Example 1

Procedure for Detection of SH Groups in Peptides and Thiolated Proteins

The presence of SH groups in peptides, thyolated proteins and products of conjugate synthesis through maleimide-sulfhydril cross-linking, and also the immobilization of peptides on gels were analyzed using known DTNB method in Tris buffer, pH 8.0, using molar absorbance $E_{412\ TNB2-}=1.37\times10^4\ cm^{-1}\ M^{-1}$.

Example 2

Conversion of Amino Groups of BSA, StrAv and HRP into Maleimide Groups

Maleimide groups were introduced into BSA (Sigma), StrAv (Scipps Lab) and HRP (Scripps Lab) using GMBS (N-(gamma-Maleimidobutiryloxy)succinimide N-Succinimidyl 4-maleimidobutyrate) in 0.1 M sodium phosphate buffer, pH 7.5, containing 1 mM EDTA at molar ratio maleimide/protein of 20:1 to 40:1 with dialysis against the same buffer with pH 6.5 as a purification step. For quantitation of the number of maleimide groups, the maleimide-modified proteins were incubated with excess of DTT and after exhaustive dialysis analyzed for presence of thiols in DTNB reaction.

The average number of maleimide groups introduced per each protein molecule was as follows: BSA-11, StrAv-7, HRP-1.1 (moles/mol protein). Protein concentration was determined spectrophotometrically using adsorption coefficients $E_{280\ nm,\ 1\ cm,\ 1\ mg/ml}=0.66$ and 3.0 for BSA and StrAv, respectively, and $E_{403\ nm,\ 1\ cm,\ 1\ mg/ml}=2.26$ for HRP.

Example 3

Blocking of SH Groups in Peptides with Maleimide

To protect Cys-peptides from oxidation and dimer formation, fresh solutions of peptides were modified with N-ethylmaleimide in 0.1M sodium phosphate, pH 6.5, with two-molar excess of maleimide. Maleimide-protected C6 and C10 were used in competition experiments as non-conjugated peptide preparations.

Example 4

Preparation of HRP with Protected Sulfhydryls and Release of Latent SH Groups

Latent SH groups were introduced into HRP using N-Succinimidyl S-acetylthiolacton (SATA) at 20–30 molar excess over HRP. Thiol groups were released using treatment with hydroxylamine hydrochloride (20 mM) with subsequent dialysis overnight against 0.1M sodium phosphate, 1 mM EDTA, pH 6.5. Thiolated HRP after analysis of SH group content was used immediately for conjugation. The average number of SH groups was 1.2 moles/mol HRP.

Example 5

Modification of BSA with Biotin and Biotin-PEG

BSA was biotinylated with Biotinamidohexanoic acid N-hydroxysuccinimidide ester at molar ratio biotin/BSA of 40:1 and with Biotin-PEG-N-hydroxisuccinimide at weight ratio BSA/Biotin-PEG-NHS of 2:1 at BSA concentration 50–100 mg/ml in 0.1 M sodium phosphate, pH 8.1. Biotinylated BSA preparations were purified by dialysis against PBS-sodium azide using dialysis membrane with cut-off 25,000 D.

Example 6

Preparation of C6-peptide and C10 Peptide Affinity Sorbents and Procedure for Affinity Antibody Purification Affinity sorbents containing C6 and C10 peptides were synthesized by coupling Cys-peptides with thiol-specific Ultralink iodoacetyl gel (Pierce) in accordance with manufacturer's recommendations. Ligand density was 0.24 mg/ml gel for C6 peptide and 0.4 mg/ml for C10 peptide.

Anti-peptide affinity antibodies were purified by passing high titer human serum (40–50 ml) from patients with Lyme disease, diluted two times with PBS-sodium azide buffer, through a column containing 3–4 ml of affinity gel at flow rate of 30 ml/hour. Columns were washed with PBS-sodium azide and bound anti-peptide antibodies eluted with Gentle™ Ag/Ab elution buffer (Pierce). Elution buffer was removed by dialysis against PBS-sodium azide or desalting on Sephadex G-25 column. Concentration of affinity antibodies was estimated spectrofotometrically using $A_{280}=1.4$ and 1.18 of 1 mg/ml solution of IgG and IgM, respectively. The yield of antibodies was 4–6 mg from 40–50 ml serum. Purity and integrity of antibody preparations was confirmed by SDS-PAGE analysis and sandwich ELISA test for detection of human IgG and IgM, using highly purified antibody calibrators (standards). Antibodies were stored at 4° C. as sterile microfiltered solutions.

Example 7

Synthesis of Peptide Conjugates with BSA, StrAv and HRP

Solutions of Maleimide-BSA (50–100 mg/ml), Maleimide-StrAv (5–7 mg/ml) and Maleimide-HRP (11–15 mg/ml) in 0.1 M sodium phosphate, 1 mM EDTA, pH 6.5, were mixed at appropriate molar ratio (in range of 0.5:1 to 8:1) with freshly prepared peptide solution in water (10 mg/ml). Molar ratio peptide/protein was calculated on the basis of peptide concentration adjusted for the content of reactive thiol groups determined in DTNB test (40–80% of total peptide). For C6 peptide (MW 2,780) 1:1 molar ratio was equivalent to 46.3 ug/mg BSA or StrAv (MW 60,000 for either protein) and 69.5 ug/mg HRP (MW 40,000). For C10 peptide (MW 1,241) 1:1 molar ratio was at 20.6 ug/mg BSA or StrAv and 31 ug/mg HRP. Mixtures were incubated for 30–60 min at room temperature. Almost 100% of thiol-peptides reacted with maleimide, as judged by DTNB test of reaction mixtures. Then, solution of beta-mercaptoethanol, 10 mg/ml in water, was added at 3–5-fold molar excess over residual maleimide groups. Conjugates were purified by dialysis against 0.1M sodium phosphate, 1 mM EDTA, pH 6.5 using dialysis membrane with cut-off 12,000–14,000 Da (to remove the fraction of unconjugated peptides that do not have reactive thiols). After dialysis, protein concentration was determined using $A_{280}$ or $A_{403}$ coefficients shown in the example. Peptide concentration in conjugate solutions was calculated assuming that all added peptide with reactive SH groups has reacted with maleimide-activated proteins (as confirmed by DTNB test), using the values of weigh ratios shown above.

Example 8

Synthesis of Peptide-BSA-HRP Conjugates

Peptide-BSA-HRP conjugates were prepared using peptide-BSA conjugates synthesized as described above, but without inactivation of residual maleimide groups with beta-mercaptoethanol. Peptide-BSA conjugates were mixed with thiolated HRP solution containing approx 1.2 SH groups per HRP molecule, prepared as described in Example 1. Molar ratios HRP/BSA were 1:1, 2:1, 3:1 and 4.5:1, based on weight ratio of 0.66 mg HRP per mg BSA for 1:1 ratio. Mixtures were incubated for 30 min, then solution of N-ethylmaleimide (1 mg/ml in water) was added in amount equivalent to amount of original thiol content in SH-HRP. Mixtures were incubated 10 min more, and finally residual maleimide groups were inactivated by addition of beta-mercaptoethanol solution (10 mg/ml in water), in slight excess to total amount of maleimide groups in reaction mixture. The concentration of peptides in conjugates was calculated from amount of peptides added into reaction as a peptide-BSA conjugate.

Example 9

Plate Coating Procedures for Bi-BSA, Bi-PEG-BSA, Peptide-BSA, StrAv-biotin-peptide Polystyrol plates (Costar HB) were coated with capture reagents from PBS-sodium azide overnight at 4–8° C. Bi-BSA and Bi-PEG-BSA (0.5–4 ug/ml) were adsorbed at 200–250 ul/well, peptide-BSA reagents (0.5–2 ug BSA/ml) and StrAv (1–2 ug/ml) were adsorbed at 100 ul/well. For blocking, PBS-0.05% Tween-20 was used for plates with biotinylated BSA, and 1% Casein-4% sucrose, pH 8.0, was used for plates with peptide-BSA or peptide-StrAv. Biotinylated peptides were immobilized on plates coated with StrAv at 0.5 ug/ml (100 ul/well) in the casein-sucrose blocking buffer. Plates were dried at room temperature overnight and stored in bags with desiccant.

Example 10

Adsorption of Capture Reagent on NC Membranes

Biotin-PEG-BSA was applied on dicks of NC membrane of 0.45 um or 1.2 um pore size (Schleicher&Schuell) installed into filtration device. Solution was prepared in PBS-azide with concentration of BSA 0.05–0.2 mg/ml, and 0.5 ml was used per 14-mm diameter disc. After aspiration of applied aliquots, discs were washed two times with 1.0 ml of PBS-0.05% Tween-20.

Biotin-PEG-BSA was striped on NC membrane (0.45 um) using Bio-Dot dispenser from PBS-azide solution at concentration 0.2–1.0 mg/ml at pump flow rate 2 ul/cm and platform speed 50 mm/sec. Membranes was dried 30–60 min at room temperature, blocked in PBS-0.05% Tween-20 for 1 hour, and dried again.

Example 11

Preparation of C6-BSA Colloidal Gold Conjugates

Colloidal gold particles (30 nm size) were prepared using standard citrate method (De Mey, 1986), pH was adjusted to 7.5 with 0.2 M potassium carbonate. Colloidal gold/C6-BSA conjugates were prepared from C6-BSA conjugates synthesized as described in Example, with beta-mercaptoehanol treatment to inactivate residual maleimide groups. C6-BSA conjugates were adsorbed at 0.5–2 ug/ml, and then blocked using PEG 15,000/BSA mixture. Amount of C6-BSA used for adsorption was slightly less than the maximum protecting concentration. Amount of bound C6-BSA was calculated assuming that all added conjugate was bound to gold particles using OD518 nm values as a measure of colloidal gold concentrations.

Example 12

Basic Format for SICS-DLA ELISA (Antibody Assay in SICS-DLA ELISA)

Test samples (0.05 ml), which may be undiluted or diluted sera, purified anti-peptide antibodies in various diluents (normal human or calf serum, PBS with casein-Tween-20), were added into wells of plates coated with biotinylated BSA as described in Example 5. Conjugate solution (0.05 ml) containing mixture of Peptide-StrAv and Peptide-HRP or Peptide-BSA-HRP (range of peptide concentration 0.01–0.16 ug/ml) in HRP/Protein Stabilizer (SurModics, Inc) was added. Plates were incubated with agitation on plate shaker/agitator for 25 min and washed four times with PBS-Tween-20. TMB substrate solution (Moss, Inc) was added (0.1 ml) and plates incubated for 4 min with agitation. Stop solution (0.1 ml of 0.1 N sulfuric acid) was added and absorbance at 450 nm was determined in ELISA plate reader blanked on air.

FIG. 1 shows the results. Highest sensitivity was obtained at ratio 0.5 Mol C6 peptide:1 Mol StrAv (0.5:1) and C6-HRP conjugates at ratio 1 Mol C6 peptide: 1 Mol HRP (1:1). The concentration of C6 peptide in conjugates mixture was 0.03 ug/ml for C6-StrAv conjugates and 0.05 ug/ml for C6-HRP conjugates. The figure insert demonstrates linearity in the dynamic range of the ELISA reader. The detection limit, calculated as antibody concentration at OD=Blank OD+50%=30 ng/ml. The total assay time was approximately 35 min.

Figure 12:
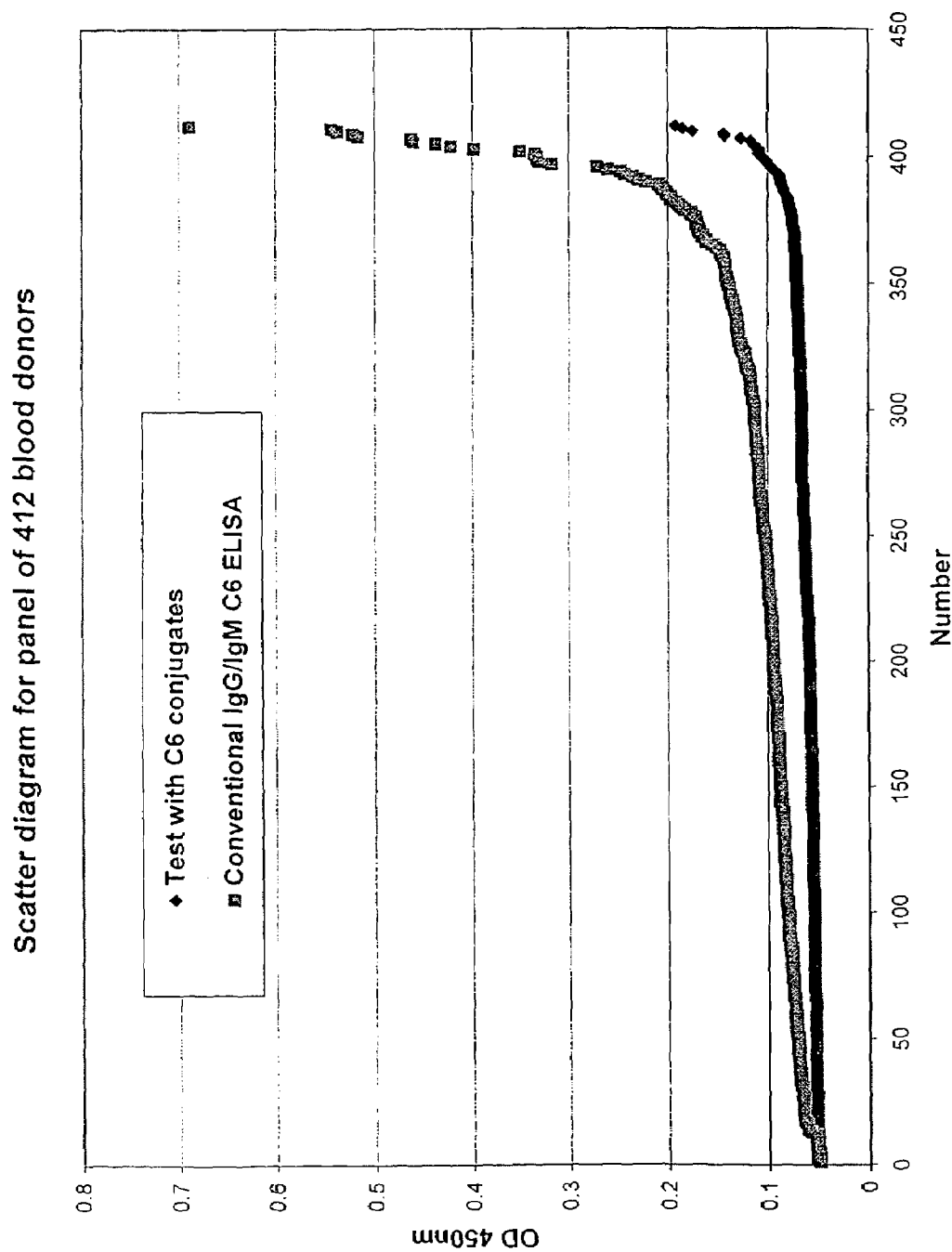
FIG. 12 shows scatter plots of OD for a panel of normal blood donors (412 samples) tested in parallel in conventional IgG/IgM C6 ELISA (at dilution 1:20) with C6 peptide immobilized on solid phase and new test on undiluted sera as described in Example 12.
Figure 13:
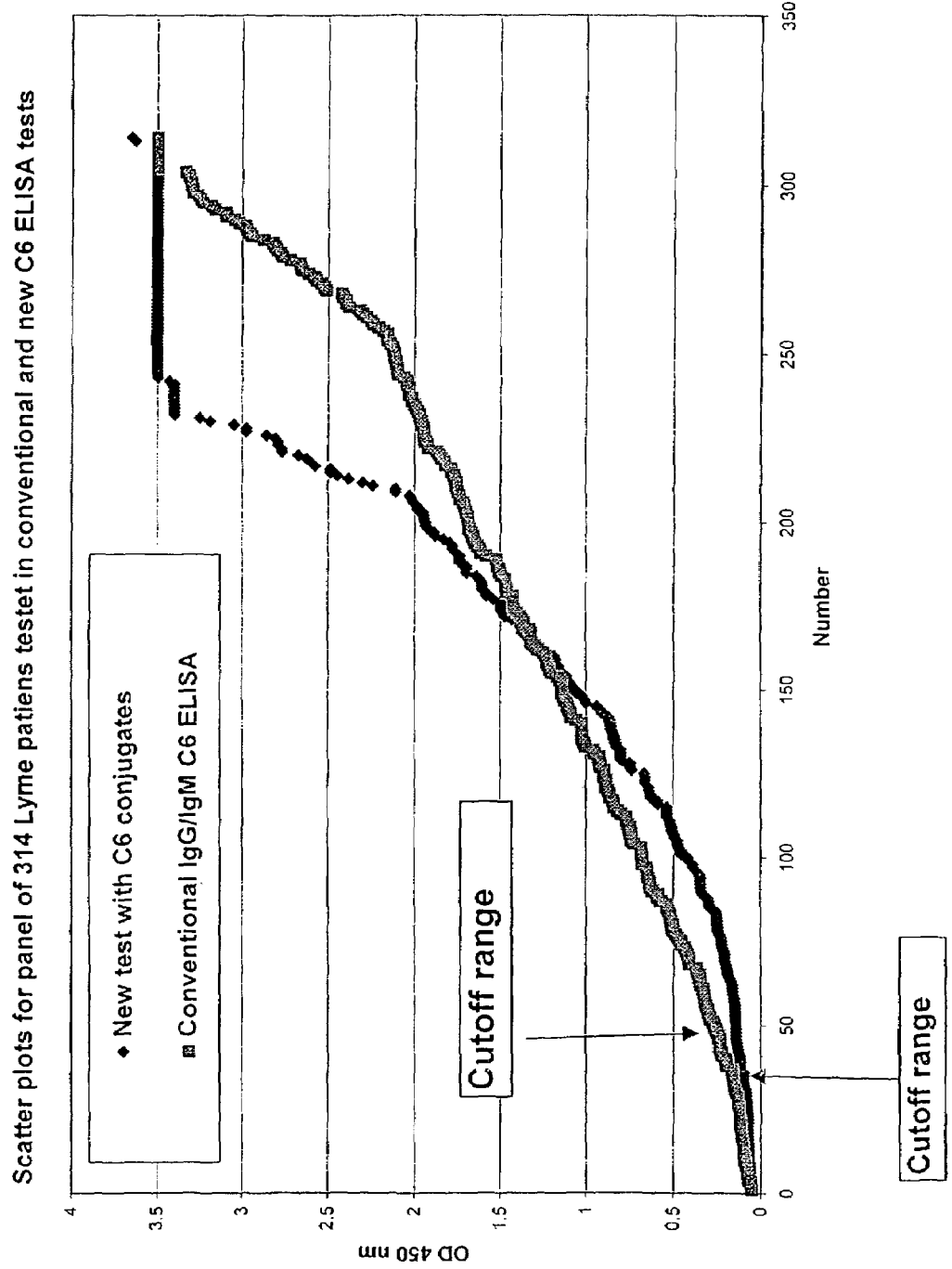
FIG. 13 shows histogram of OD distribution for panel of 314 samples of Lyme patients or patients with suspected Lyme disease tested in parallel in conventional IgG/IgM C6 ELISA test at dilution 1:20 and with new test (Example 12) on undiluted samples. The number of samples which have a high OD values including OVER were significantly higher for new test which demonstrates the high analytical sensitivity of a new test.
Figure 14:
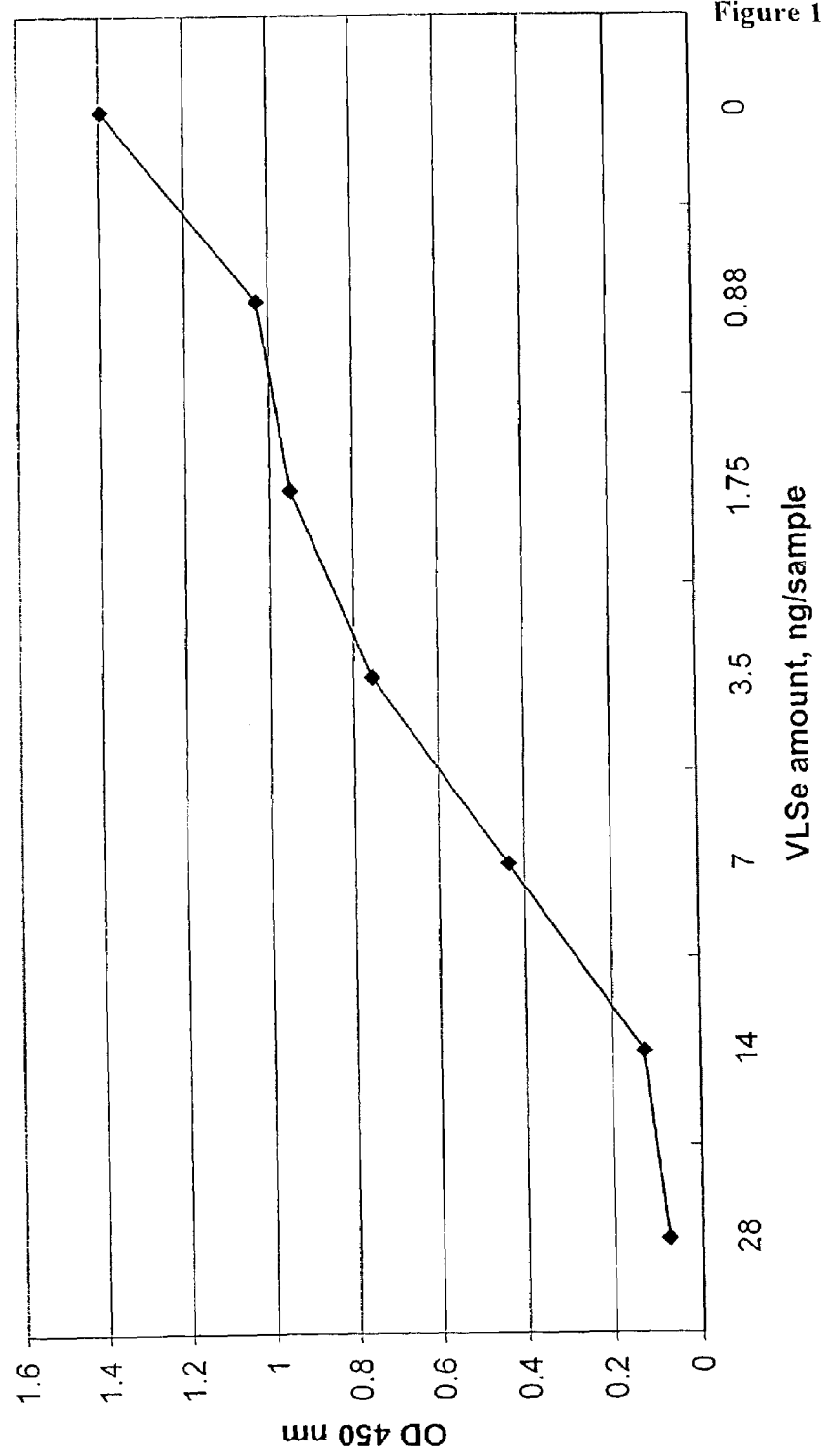
FIG. 14 shows the application of C6-conjugates in a competitive format for the detection of whole protein (rec VLSe) containing C6 peptide. Less than 1 ng whole VLSe in a sample can be detected by this method.

FIG. 12 shows scatter plots of OD for a panel of normal blood donors (412 samples) tested in parallel in conventional IgG/IgM C6 ELISA (at dilution 1:20) with C6 peptide immobilized on solid phase and new test on undiluted sera as described in above. Very low OD values obtained for these normal samples in the new test were practically indistinguishable from the OD of the blank. Cutoff values were calculated as average OD plus 3 standard deviations. The cutoff value for the new test was 0.11 and 0.35 for conventional test.

Example 13

Basic Format for Conventional ELISA Using Anti-human IgG/IgM Conjugates

Test samples (0.1 ml) containing 1:20 diluted sera in casein-Tween-20 diluent were added into plates coated with peptide-BSA conjugates or biotinylated peptides through StrAv bridge as described in Examples 9. Plates were incubated still at room temperature for 30 min and washed three times with PBS-Tween-20. Conjugate solution (0.1 ml) containing goat anti-human IgG, IgM or IgG/IgM (Jackson Immunoresearch Lab) at 0.16 ug/ml in StabilZyme HRP (SurModics, Inc) was added. Plates were incubated for 20 min at room temperature and washed four times. TMB ELISA substrate (0.1 ml) was added and plates were incubated for 4 min before stopping with 0.1 ml of 0.1 N sulfuric acid. Absorbance at 450 nm was measured in plate reader blanked on air.

Example 14

Analysis of Competition Between Immobilized Peptides and Peptides in Solution for Binding to Anti-peptide Antibodies Plates were coated with peptide-BSA conjugates at molar ratio peptide-BSA of 2:1 as described in Example 7. Samples containing known amount of anti-peptide antibodies (in a range 0.1–1.6 ug/ml) were first pre-incubated in separate tubes for 20 min with serially diluted peptides or peptide conjugates (in a peptide concentration range 0.006–280 ug/ml). Than, 0.1 ml aliquots were transferred into plates coated with peptide conjugates. Plates were incubated for 30 min and washed three times. Conjugate solution containing human IgG- or IgM-specific conjugate was added as described in Example 13. Further steps were as in Example 13.

Example 15

Procedure for Flow-through Test with HRP Label

Samples (200 ul) were prepared from microfiltered Positive control serum of IgG/IgM C6 ELISA test (Immunetics) by dilution with normal calf serum. Equal volume of C6 conjugate mixture (C6-StrAv, 0.5:1, 0.03 ug/ml, and C6-HRP, 1:1, 0.05 ug/ml) was added to samples. After incubation for 5–10 min, the sample-conjugates mixture was applied on discs of NC membrane (0.45 um) coated with Bi-PEG-BSA as described in Example 9. After short incubation (1 min), liquid was filtered through membrane by applying positive pressure on the top. Membranes were washed three times with 1 ml PBS-Tween-20. Then, 0.5 ml of TMB precipitating membrane substrate (Moss, Inc) was added. After 2 min, the substrate was filtered and membranes washed with water.

Example 16

Procedure for Flow-through Test with Colloidal Gold Label

Samples described in Example 15 were mixed with conjugates (C6-StrAv, 0.5:1, 0.1 ug/ml and C6-BSA (2:1)-Gold, 0.05 ug/ml) and incubated for 30 min with agitation. Mixtures were then applied on discs of NC membrane (1.2 um), coated with Bi-PEG-BSA as described in Example 10, installed into filtration device and incubated for another 5 min before completion of filtration. Discs were washed two times with PBS-Tween-20.

Example 17

Procedure for Dot-blot Test with HRP Label

Samples (0.25 ml) were mixed with equal volume of C6 conjugates as described in Example 15, and placed in a microtray. Strips of NC membrane with applied Bi-PEG-BSA as described in Example 10 were placed into sample-conjugate mixtures and incubated with agitation for 30 min. After complete aspiration of liquid, strips were washed three times with 2 ml PBS-Tween-20 and once with water. TMB membrane ELISA substrate was added and strips incubated for 4 min with agitation. Finally, the substrate was aspirated and membranes rinsed with water.

Example 18

Procedure for Dot-blot Test with Colloidal Gold Label

Strips containing Bi-PEG-BSA lines were prepared as in Example 10 and were placed into microtrays containing 0.5 ml sera samples prepared from Positive control as in Example 15. A mixture of C6-StrAv and C6-BSA-Gold conjugates was added. Final concentration of C6 peptide was as described in Example 16. Mixtures were incubated with agitation for 45 min, than washed with PBS-tween-20.

Example 19

Competitive Assay for Antigen Detection Using Peptide Conjugates

Samples containing known amount of recombinant VLSe (0.045 ml) were placed into wells coated with Bi-PEG-BSA as described in Example 9. Solution of anti-C6 IgG (10 ug/ml was added at 0.05 ul/well. Mixtures were incubated for 10 min with agitation and 0.05 ml of conjugate solution containing 0.03 ug/ml C6-StrAv (0.5:1) and 0.05 ug/ml C6-HRP (1:1) was added. Plates were incubated with agitation for 25 min, washed four times with PBS-tween-20, and bound HRP was detected as described in Example 13.

Example 20

Analysis of Antibody Classes Involved in Specific Immune Complex with Labeled Peptide Antigens Samples of human patients sera (0.05 ul) were diluted in coated well prepared as described in Example 12 with 0.045 ml calf serum (Sigma) or Casein-tween-20 diluent. Conjugate solution (0.05 ml) containing mixture of peptide-StrAv plus peptide-HRP at concentration described in Example 12 was added. The mixture were incubated for 25 min and agitation, aspirated and washed 3 times with PBS-tween. Solution of Goat-anti-human IgG or IgM-HRP at concentration 0.08 ug/ml was added and plates were incubated for 15 min at agitation. After washing (four times) bound HRP was detected using standard procedure for TMB ELISA substrate as described in Example 13.

EQUIVALENTS

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

I claim:

1. A kit comprising
   a first component comprising biotin linked, through a polyethylene glycol spacer, to albumin,
   a second component comprising a biotin-binding moiety conjugated to an antigen or hapten that binds an anti-microbial antibody to be detected in a sample, and
   a third component comprising the antigen or hapten conjugated to a label.

2. The kit of claim 1, wherein the second and third components are supplied as dry samples or liquid samples, wherein the dry or liquid samples may be separate or mixtures of the second and third components.

3. The kit of claim 1, wherein the second and third components comprise more than one antigen or hapten molecule.

4. The kit of claim 1, wherein the second component and the third component each comprise two or more different antigens or haptens that are chemically linked to the biotin-binding moiety or the detector label, respectively.

5. The kit of claim 1, wherein the biotin-binding moiety is avidin or streptavidin.

6. The kit of claim 1, wherein the sample is taken from a human or animal having a microbial infection.

7. The kit claim 6, wherein the microbial infection is Lyme disease.

8. The kit of claim 1, wherein the antigen is C6 peptide derived from VLSe protein of *B. burgdorferi*.

9. The kit of claim 1, wherein the antigen is C10 peptide derived from OspC protein of *B. burgdorferi*.

10. The kit of claim 1, wherein the antigens are peptides derived from VLSe protein (C6) and OspC protein (C10) of *B. burgdorferi*.

11. The kit of claim 1, further comprising instructions for practicing the method of detecting an antibody in a sample.

12. A kit comprising
    a solid support to which is noncovalently adsorbed a first component comprising biotin linked, through a polyethylene glycol spacer, to albumin;
    a second component comprising a biotin-binding moiety conjugated to an antigen or hapten that binds an anti-microbial antibody to be detected in a sample; and
    a third component comprising the antigen or hapten conjugated to a label.

13. A kit of claim 12 wherein the second and third components are present in a single reagent mixture.

* * * * *